US012295930B2

(12) United States Patent
Naqvi et al.

(10) Patent No.: US 12,295,930 B2
(45) Date of Patent: May 13, 2025

(54) INDUCING PROLIFERATION OF CARDIOMYOCYTES AND THERAPEUTIC USES RELATED THERETO

(71) Applicant: Emory University, Atlanta, GA (US)

(72) Inventors: Nawazish Naqvi, Lilburn, GA (US); Ahsan Husain, Atlanta, GA (US)

(73) Assignee: Emory University, Atlanta, GA (US)

( * ) Notice: Subject to any disclaimer, the term of this patent is extended or adjusted under 35 U.S.C. 154(b) by 891 days.

(21) Appl. No.: 17/268,590

(22) PCT Filed: Aug. 14, 2019

(86) PCT No.: PCT/US2019/046566
§ 371 (c)(1),
(2) Date: Feb. 15, 2021

(87) PCT Pub. No.: WO2020/037076
PCT Pub. Date: Feb. 20, 2020

(65) Prior Publication Data

US 2021/0299078 A1 Sep. 30, 2021

Related U.S. Application Data

(60) Provisional application No. 62/718,583, filed on Aug. 14, 2018, provisional application No. 62/813,467, filed on Mar. 4, 2019.

(51) Int. Cl.

| | |
|---|---|
| ***C12N 15/11*** | (2006.01) |
| ***A61K 31/138*** | (2006.01) |
| ***A61K 31/198*** | (2006.01) |
| ***A61K 31/403*** | (2006.01) |
| ***A61K 31/713*** | (2006.01) |
| ***A61K 38/17*** | (2006.01) |
| ***A61K 38/18*** | (2006.01) |
| ***A61K 38/30*** | (2006.01) |
| ***A61K 45/06*** | (2006.01) |
| ***A61P 9/04*** | (2006.01) |
| ***C12N 9/16*** | (2006.01) |
| ***C12N 15/113*** | (2010.01) |

(52) U.S. Cl.
CPC .......... *A61K 31/198* (2013.01); *A61K 31/138* (2013.01); *A61K 31/403* (2013.01); *A61K 31/713* (2013.01); *A61K 38/179* (2013.01); *A61K 38/1883* (2013.01); *A61K 38/30* (2013.01); *A61K 45/06* (2013.01); *A61P 9/04* (2018.01); *C12N 9/16* (2013.01); *C12N 15/1137* (2013.01); *C12N 2310/14* (2013.01)

(58) Field of Classification Search
None
See application file for complete search history.

(56) References Cited

U.S. PATENT DOCUMENTS

| | | | | |
|---|---|---|---|---|
| 5,643,939 | A | 7/1997 | Ohlstein | |
| 2006/0160733 | A1 | 7/2006 | Chaukhry | |
| 2007/0031844 | A1* | 2/2007 | Khvorova | A61P 3/10 435/6.13 |
| 2007/0276135 | A1 | 11/2007 | Khivorova | |
| 2010/0166827 | A1 | 7/2010 | Kuhn | |
| 2013/0244262 | A1 | 9/2013 | Yamashita | |
| 2016/0113889 | A1 | 4/2016 | Day | |
| 2017/0368140 | A1* | 12/2017 | Zhou | A61K 38/18 |
| 2018/0000778 | A1 | 1/2018 | Ramchandran | |

OTHER PUBLICATIONS

D'Uva, G., Aharonov, A., Lauriola, M. et al. ERBB2 triggers mammalian heart regeneration by promoting cardiomyocyte dedifferentiation and proliferation. Nat Cell Biol, 2015, 17, 627-638 (Year: 2015).*
Zhang, Gui-sheng; Qu, Ling-ling; Yu, Hua; Zhang, Ting-ting; Li, Long-gui. Clinical observation of congestive heart failure treated by metoprolol assisted with low dose of thyroid hormone. Linchuang Huicui, 2011, 26(24):2120-2122. Abstract only. (Year: 2011).*
Arnold, Anne-Sophie; Tang, Yao Liang; Qian, K.; Shen, Leping; Valencia, V.; Phillips, Michael I.; Zhang, Yuan C. Specific β1-adrenergic receptor silencing with small interfering RNA lowers high blood pressure and improves cardiac function in myocardial ischemia. J. Hypertension, 2007, 25(1):197-205 (Year: 2007).*
Enzo R. Porrello et al. , Transient Regenerative Potential of the Neonatal Mouse Heart. Science, 2011, 331:1078-1080 (Year: 2011).*
Chattergoon NN, Giraud GD, Louey S, Stork P, Fowden AL, Thornburg KL. Thyroid hormone drives fetal cardiomyocyte maturation. FASEB J. Jan. 2012;26(1):397-408. (Year: 2012).*
Alkass et al. No Evidence for Cardiomyocyte Number Expansion in Preadolescent Mice, Cell, 2015, 163, 1026-1036.
Animal Resources Centre. Rat and Mice Weights, Jul. 2018 [online] [Retrieved on Oct. 17, 2019]. Retrieved from the Internet< URL: https://web.archive.org/web/20180717224335/https://www.arc.wa.gov.au/?page_id=125 > p. 2 to 3.
Arnold et al. Specific B1-adrenergic receptor silencing with small interfering RNA lowers high blood pressure and improves cardiac function in myocardial ischemia. J Hypertens 25:197-205, 2007.
Bogush et al. Dusp5 Triggers and Maintains Cell Cycle Block in Postnatal Cardiomyocytes, Circulation, 2019, 140, Abstract 12291.
Bogush et al. DUSP5 expression in left ventricular cardiomyocytes of young hearts regulates thyroid hormone (T3)-induced proliferative ERK1/2 signaling, Scientific Reports, 2020, 10:21918.

(Continued)

*Primary Examiner* — Ekaterina Poliakova-Georgantas
(74) *Attorney, Agent, or Firm* — Emory Patent Group

(57) ABSTRACT

This disclosure relates to methods of treating or preventing heart malformations or cardiovascular diseases comprising administering an effective amount of thyroid hormone in combination with i) an agent that decreases DUSP5 and/or DUSP6 expression and/or ii) a beta-adrenergic blocking agent to a subject in need thereof. In certain embodiments, this disclosure relates to in vivo and in vitro methods of inducing proliferation of cardiomyocytes using agents or combinations of agents disclosed herein.

12 Claims, 8 Drawing Sheets

Specification includes a Sequence Listing.

(56) References Cited

OTHER PUBLICATIONS

Cai et al. Repair Injured Heart by Regulating Cardiac Regenerative Signals, Stem Cells International, vol. 2016, Article ID 6193419, 17 pages.
Chattergoon et al. Thyroid hormone drives fetal cardiomyocyte maturation, FASEB J. 26, 397-408 (2012).
Chattergoon et al. Thyroid hormone signaling and consequences for cardiac development, Journal of Endocrinology, 2019, 242, T145-T160.
Chimenti et al. B-blockers treatment of cardiac surgery patients enhances isolation and improves phenotype of cardiosphere-derived cells, Scientific Reports, 6:36774, 2016.
Deng et al. Triiodothyronine promotes the proliferation of epicardial progenitor cells through the MAPK/ERK pathway, Biochemical and Biophysical Research Communications 486 (2017) 372-377.
Deng et al. Autonomous and Growth Factor—Induced Hypertrophy in Cultured Neonatal Mouse Cardiac Myocytes Comparison With Rat, Circ Res. 2000, 87:781-788.
D'Uva et al. ERBB2 triggers mammalian heart regeneration by promoting cardiomyocyte dedifferentiation and proliferation, Nature Cell Biology, 2015, vol. 17, No. 5, 627.
Extended European Search Report, EP Application No. 19849768.1, National Stage application PCT/US2019046566, Dated Apr. 21, 2022.
Ferguson et al. Signal-dependent repression of DUSP5 by class I HDACs controls nuclear ERK activity and cardiomyocyte hypertrophy, PNAS, 2013, 110, 24, 9807.
Foglia et al. Building and re-building the heart by cardiomyocyte proliferation, Development. 2016, 143(5): 729-740.
Hirose et al. Evidence for hormonal control of heart regenerative capacity during endothermy acquisition, Science 364, 184-188 (2019).
Li et al. Thyroid hormone action in postnatal heart development, Stem Cell Research (2014) 13, 582-591.
Maillet et al. DUSP6 (MKP3) Null Mice Show Enhanced ERK1/2 Phosphorylation at Baseline and Increased Myocyte Proliferation in the Heart Affecting Disease Susceptibility, The Journal of Biological Chemistry, 2008, vol. 283, No. 45, pp. 31246-31255.
Missinato et al. Dusp6 attenuates Ras/MAPK signaling to limit zebrafish heart regeneration, Development (2018) 145, dev157206.
Molina et al. Zebrafish chemical screening reveals an inhibitor of Dusp6 that expands cardiac cell lineages, Nat Chem Biol, 2009, 5(9): 680-687.
Nagele et al. Combination therapy with carvedilol and amiodarone in patients with severe heart failure, European Journal of Heart Failure 2 (2000) 71-79.
Nakada et al. Hypoxia induces heart regeneration in adult mice, Nature, vol. 541, pp. 222-227 (2017).
Naqvi et al. A Proliferative Burst During Preadolescence Establishes the Final Cardiomyocyte Number., Cell. 2014, 157(4): 795-807.
Neumann et al. Identification of inhibitors that target dual-specificity phosphatase 5 provide new insights into the binding requirements for the two phosphate pockets, BMC Biochemistry (2015) 16:19.
Park et al. Discovery of Novel DUSP4 Inhibitors through the Virtual Screening with Docking Simulations, Bull. Korean Chem. Soc. 2014, vol. 35, No. 9, 2655.
Porrello et al. Transient Regenerative Potential of the Neonatal Mouse Heart, Science. 2011, 331(6020): 1078-1080.
Razvi et al. Thyroid Hormones and Cardiovascular Function and Diseases, J Am Coll Cardiol. 2018, 71 (16):1781-1796.
Tan et al. Redox activation of JNK2a2 mediates thyroid hormonestimulated proliferation of neonatal murine cardiomyocytes, Scientific Reports, 2019, 9:17731.
Tan et al. Thyroid hormone plus dual-specificity phosphatase-5 siRNA increases the number of cardiac muscle cells and improves left ventricular contractile function in chronic doxorubicin-injured hearts, Theranostics, 2021, 11(10):4790-480.
Torborg et al. Mayo Clinic Q and A: How long do you need beta blockers after a heart attack? 2018, Available at https://newsnetwork.mayoclinic.org/discussion/mayo-clinic-q-and-a-how-long-do-you-need-beta-blockers-after-a-heart-attack/.
Tseng et al. B-Adrenergic receptors (bAR) regulate cardiomyocyte proliferation during early postnatal life, FASEB J. 2001, 15(11):1921-6.
Ueda et al. Dual-specificity phosphatase 5 (DUSP5) as a direct transcriptional target of tumor suppressor p53, Oncogene (2003) 22, 5586-5591.
Uygur et al. Mechanisms of Cardiac Regeneration, Developmental Cell, 36, 2016.
Xu et al. Inhibition of HDAC3 prevents diabetic cardiomyopathy in OVE26 mice via epigenetic regulation of DUSP5-ERK1/2 pathway, Clinical Science (2017) 131 1841-1857.
Yester et al. Mechanisms of Cardiomyocyte Proliferation and Differentiation on Development and Regeneration, Curr Cardiol Rep, 2017, 19(2):13.
European Examination report for EP application No. 19849768.7, dated Mar. 24, 2025.

* cited by examiner

SEQUENCE LISTING

<160> NUMBER OF SEQ ID NOS: 120

<210> SEQ ID NO 1
<211> LENGTH: 19
<212> TYPE: DNA
<213> ORGANISM: Artificial
<220> FEATURE:
<223> OTHER INFORMATION: Synthetic construct

<400> SEQUENCE: 1
aaacccauuu cacaagaga 19

<210> SEQ ID NO 2
<211> LENGTH: 19
<212> TYPE: DNA
<213> ORGANISM: Artificial
<220> FEATURE:
<223> OTHER INFORMATION: Synthetic construct

<400> SEQUENCE: 2
aaacugggau ggaggaauc 19

<210> SEQ ID NO 3
<211> LENGTH: 19
<212> TYPE: DNA
<213> ORGANISM: Artificial
<220> FEATURE:
<223> OTHER INFORMATION: Synthetic construct

<400> SEQUENCE: 3
aagagaagau ugagaguga 19

<210> SEQ ID NO 4
<211> LENGTH: 19
<212> TYPE: DNA
<213> ORGANISM: Artificial
<220> FEATURE:
<223> OTHER INFORMATION: Synthetic construct

<400> SEQUENCE: 4
aagcacaauu uccaccuua 19

<210> SEQ ID NO 5
<211> LENGTH: 19
<212> TYPE: DNA
<213> ORGANISM: Artificial
<220> FEATURE:
<223> OTHER INFORMATION: Synthetic construct

<400> SEQUENCE: 5
aaggaaggcc aagccauua 19

<210> SEQ ID NO 6
<211> LENGTH: 19
<212> TYPE: DNA
<213> ORGANISM: Artificial
<220> FEATURE:
<223> OTHER INFORMATION: Synthetic construct

<400> SEQUENCE: 6
aaggguacuu gcuagguau 19

<210> SEQ ID NO 7
<211> LENGTH: 19
<212> TYPE: DNA
<213> ORGANISM: Artificial

-continued

<220> FEATURE:
<223> OTHER INFORMATION: Synthetic construct

<400> SEQUENCE: 7
acccugaaau guuguguag 19

<210> SEQ ID NO 8
<211> LENGTH: 19
<212> TYPE: DNA
<213> ORGANISM: Artificial
<220> FEATURE:
<223> OTHER INFORMATION: Synthetic construct

<400> SEQUENCE: 8
acuguggacu ucugggauu 19

<210> SEQ ID NO 9
<211> LENGTH: 19
<212> TYPE: DNA
<213> ORGANISM: Artificial
<220> FEATURE:
<223> OTHER INFORMATION: Synthetic construct

<400> SEQUENCE: 9
agacuuucua cucggaaua 19

<210> SEQ ID NO 10
<211> LENGTH: 19
<212> TYPE: DNA
<213> ORGANISM: Artificial
<220> FEATURE:
<223> OTHER INFORMATION: Synthetic construct

<400> SEQUENCE: 10
agaguucgcc uuuucauuu 19

<210> SEQ ID NO 11
<211> LENGTH: 19
<212> TYPE: DNA
<213> ORGANISM: Artificial
<220> FEATURE:
<223> OTHER INFORMATION: Synthetic construct

<400> SEQUENCE: 11
agcaggcucu ucacugaua 19

<210> SEQ ID NO 12
<211> LENGTH: 19
<212> TYPE: DNA
<213> ORGANISM: Artificial
<220> FEATURE:
<223> OTHER INFORMATION: Synthetic construct

<400> SEQUENCE: 12
agucauacuu gaacuuguc 19

<210> SEQ ID NO 13
<211> LENGTH: 19
<212> TYPE: DNA
<213> ORGANISM: Artificial
<220> FEATURE:
<223> OTHER INFORMATION: Synthetic construct

<400> SEQUENCE: 13
aguguugcgu ggauguaaa 19

-continued

<210> SEQ ID NO 14
<211> LENGTH: 19
<212> TYPE: DNA
<213> ORGANISM: Artificial
<220> FEATURE:
<223> OTHER INFORMATION: Synthetic construct

<400> SEQUENCE: 14
caaauggauc ccuguggaa 19

<210> SEQ ID NO 15
<211> LENGTH: 19
<212> TYPE: DNA
<213> ORGANISM: Artificial
<220> FEATURE:
<223> OTHER INFORMATION: Synthetic construct

<400> SEQUENCE: 15
caacggccac auccugcua 19

<210> SEQ ID NO 16
<211> LENGTH: 19
<212> TYPE: DNA
<213> ORGANISM: Artificial
<220> FEATURE:
<223> OTHER INFORMATION: Synthetic construct

<400> SEQUENCE: 16
caacguggga gaaagaagu 19

<210> SEQ ID NO 17
<211> LENGTH: 19
<212> TYPE: DNA
<213> ORGANISM: Artificial
<220> FEATURE:
<223> OTHER INFORMATION: Synthetic construct

<400> SEQUENCE: 17
caagagcaac ugugauuuu 19

<210> SEQ ID NO 18
<211> LENGTH: 19
<212> TYPE: DNA
<213> ORGANISM: Artificial
<220> FEATURE:
<223> OTHER INFORMATION: Synthetic construct

<400> SEQUENCE: 18
caauaaauac cugcagcaa 19

<210> SEQ ID NO 19
<211> LENGTH: 19
<212> TYPE: DNA
<213> ORGANISM: Artificial
<220> FEATURE:
<223> OTHER INFORMATION: Synthetic construct

<400> SEQUENCE: 19
caauacugaa gaccucauu 19

<210> SEQ ID NO 20
<211> LENGTH: 19
<212> TYPE: DNA
<213> ORGANISM: Artificial
<220> FEATURE:
<223> OTHER INFORMATION: Synthetic construct

<400> SEQUENCE: 20
cacaauuucc accuuauuu 19

<210> SEQ ID NO 21
<211> LENGTH: 19
<212> TYPE: DNA
<213> ORGANISM: Artificial
<220> FEATURE:
<223> OTHER INFORMATION: Synthetic construct

<400> SEQUENCE: 21
caccaggcuu gcaaaugaa 19

<210> SEQ ID NO 22
<211> LENGTH: 19
<212> TYPE: DNA
<213> ORGANISM: Artificial
<220> FEATURE:
<223> OTHER INFORMATION: Synthetic construct

<400> SEQUENCE: 22
caccuacacu acaaaugga 19

<210> SEQ ID NO 23
<211> LENGTH: 19
<212> TYPE: DNA
<213> ORGANISM: Artificial
<220> FEATURE:
<223> OTHER INFORMATION: Synthetic construct

<400> SEQUENCE: 23
cagcaacgug ggagaaaga 19

<210> SEQ ID NO 24
<211> LENGTH: 19
<212> TYPE: DNA
<213> ORGANISM: Artificial
<220> FEATURE:
<223> OTHER INFORMATION: Synthetic construct

<400> SEQUENCE: 24
cagcagaagc ccuguggca 19

<210> SEQ ID NO 25
<211> LENGTH: 19
<212> TYPE: DNA
<213> ORGANISM: Artificial
<220> FEATURE:
<223> OTHER INFORMATION: Synthetic construct

<400> SEQUENCE: 25 cagggguggcc caguugaaa 19

<210> SEQ ID NO 26
<211> LENGTH: 19
<212> TYPE: DNA
<213> ORGANISM: Artificial
<220> FEATURE:
<223> OTHER INFORMATION: Synthetic construct

<400> SEQUENCE: 26
cauggucucg cccaacuuu 19

<210> SEQ ID NO 27

-continued

<211> LENGTH: 19
<212> TYPE: DNA
<213> ORGANISM: Artificial
<220> FEATURE:
<223> OTHER INFORMATION: Synthetic construct

<400> SEQUENCE: 27
cauuagcucc cacuuucaa 19

<210> SEQ ID NO 28
<211> LENGTH: 19
<212> TYPE: DNA
<213> ORGANISM: Artificial
<220> FEATURE:
<223> OTHER INFORMATION: Synthetic construct

<400> SEQUENCE: 28
cauuccaccu cuucucaga 19

<210> SEQ ID NO 29
<211> LENGTH: 19
<212> TYPE: DNA
<213> ORGANISM: Artificial
<220> FEATURE:
<223> OTHER INFORMATION: Synthetic construct

<400> SEQUENCE: 29
ccaagagcaa cugugauuu 19

<210> SEQ ID NO 30
<211> LENGTH: 19
<212> TYPE: DNA
<213> ORGANISM: Artificial
<220> FEATURE:
<223> OTHER INFORMATION: Synthetic construct

<400> SEQUENCE: 30
ccaagcaguu ccgccugaa 19

<210> SEQ ID NO 31
<211> LENGTH: 19
<212> TYPE: DNA
<213> ORGANISM: Artificial
<220> FEATURE:
<223> OTHER INFORMATION: Synthetic construct

<400> SEQUENCE: 31
ccacacggcu gacauuagc 19

<210> SEQ ID NO 32
<211> LENGTH: 19
<212> TYPE: DNA
<213> ORGANISM: Artificial
<220> FEATURE:
<223> OTHER INFORMATION: Synthetic construct

<400> SEQUENCE: 32
ccaccuacac uacaaaugg 19

<210> SEQ ID NO 33
<211> LENGTH: 19
<212> TYPE: DNA
<213> ORGANISM: Artificial
<220> FEATURE:
<223> OTHER INFORMATION: Synthetic construct

<400> SEQUENCE: 33

-continued ccacuuucaa gaagcaaua 19

<210> SEQ ID NO 34
<211> LENGTH: 19
<212> TYPE: DNA
<213> ORGANISM: Artificial
<220> FEATURE:
<223> OTHER INFORMATION: Synthetic construct

<400> SEQUENCE: 34
ccauuucaca agagaagau 19

<210> SEQ ID NO 35
<211> LENGTH: 19
<212> TYPE: DNA
<213> ORGANISM: Artificial
<220> FEATURE:
<223> OTHER INFORMATION: Synthetic construct

<400> SEQUENCE: 35
cccaagagca acugugauu 19

<210> SEQ ID NO 36
<211> LENGTH: 19
<212> TYPE: DNA
<213> ORGANISM: Artificial
<220> FEATURE:
<223> OTHER INFORMATION: Synthetic construct

<400> SEQUENCE: 36
ccugaaaugu uguguagac 19

<210> SEQ ID NO 37
<211> LENGTH: 19
<212> TYPE: DNA
<213> ORGANISM: Artificial
<220> FEATURE:
<223> OTHER INFORMATION: Synthetic construct

<400> SEQUENCE: 37
cggaauaucc ugaguguug 19

<210> SEQ ID NO 38
<211> LENGTH: 19
<212> TYPE: DNA
<213> ORGANISM: Artificial
<220> FEATURE:
<223> OTHER INFORMATION: Synthetic construct

<400> SEQUENCE: 38
cuaagacccg ugugaaugu 19

<210> SEQ ID NO 39
<211> LENGTH: 19
<212> TYPE: DNA
<213> ORGANISM: Artificial
<220> FEATURE:
<223> OTHER INFORMATION: Synthetic construct

<400> SEQUENCE: 39
cugcauggcu uaccuuaug 19

<210> SEQ ID NO 40
<211> LENGTH: 19
<212> TYPE: DNA

<213> ORGANISM: Artificial
<220> FEATURE:
<223> OTHER INFORMATION: Synthetic construct

<400> SEQUENCE: 40
gaagaaaagc aguauguua 19

<210> SEQ ID NO 41
<211> LENGTH: 19
<212> TYPE: DNA
<213> ORGANISM: Artificial
<220> FEATURE:
<223> OTHER INFORMATION: Synthetic construct

<400> SEQUENCE: 41
gaagaccuca uucugucau 19

<210> SEQ ID NO 42
<211> LENGTH: 19
<212> TYPE: DNA
<213> ORGANISM: Artificial
<220> FEATURE:
<223> OTHER INFORMATION: Synthetic construct

<400> SEQUENCE: 42
gaagauugag agugagaga 19

<210> SEQ ID NO 43
<211> LENGTH: 19
<212> TYPE: DNA
<213> ORGANISM: Artificial
<220> FEATURE:
<223> OTHER INFORMATION: Synthetic construct

<400> SEQUENCE: 43
gaagcacaau uuccaccuu 19

<210> SEQ ID NO 44
<211> LENGTH: 19
<212> TYPE: DNA
<213> ORGANISM: Artificial
<220> FEATURE:
<223> OTHER INFORMATION: Synthetic construct

<400> SEQUENCE: 44
gaaggaaggc caagccauu 19

<210> SEQ ID NO 45
<211> LENGTH: 19
<212> TYPE: DNA
<213> ORGANISM: Artificial
<220> FEATURE:
<223> OTHER INFORMATION: Synthetic construct

<400> SEQUENCE: 45
gaaggguacu ugcuaggua 19

<210> SEQ ID NO 46
<211> LENGTH: 19
<212> TYPE: DNA
<213> ORGANISM: Artificial
<220> FEATURE:
<223> OTHER INFORMATION: Synthetic construct

<400> SEQUENCE: 46
gacauuagcu cccacuuuc 19

<210> SEQ ID NO 47
<211> LENGTH: 19
<212> TYPE: DNA
<213> ORGANISM: Artificial
<220> FEATURE:
<223> OTHER INFORMATION: Synthetic construct

<400> SEQUENCE: 47
gacuuuggca ugauucuua 19

<210> SEQ ID NO 48
<211> LENGTH: 19
<212> TYPE: DNA
<213> ORGANISM: Artificial
<220> FEATURE:
<223> OTHER INFORMATION: Synthetic construct

<400> SEQUENCE: 48
gagaaaaggc aguuaugaa 19

<210> SEQ ID NO 49
<211> LENGTH: 19
<212> TYPE: DNA
<213> ORGANISM: Artificial
<220> FEATURE:
<223> OTHER INFORMATION: Synthetic construct

<400> SEQUENCE: 49
gagaagauug agagugaga 19

<210> SEQ ID NO 50
<211> LENGTH: 19
<212> TYPE: DNA
<213> ORGANISM: Artificial
<220> FEATURE:
<223> OTHER INFORMATION: Synthetic construct

<400> SEQUENCE: 50
gagacuuucu acucggaau 19

<210> SEQ ID NO 51
<211> LENGTH: 19
<212> TYPE: DNA
<213> ORGANISM: Artificial
<220> FEATURE:
<223> OTHER INFORMATION: Synthetic construct

<400> SEQUENCE: 51
gaggcaaggu ccuggucca 19

<210> SEQ ID NO 52
<211> LENGTH: 19
<212> TYPE: DNA
<213> ORGANISM: Artificial
<220> FEATURE:
<223> OTHER INFORMATION: Synthetic construct

<400> SEQUENCE: 52
gagguaguug guugaagua 19

<210> SEQ ID NO 53
<211> LENGTH: 19
<212> TYPE: DNA
<213> ORGANISM: Artificial
<220> FEATURE:

-continued

<223> OTHER INFORMATION: Synthetic construct

<400> SEQUENCE: 53
gaguguugcg uggauguaa 19

<210> SEQ ID NO 54
<211> LENGTH: 19
<212> TYPE: DNA
<213> ORGANISM: Artificial
<220> FEATURE:
<223> OTHER INFORMATION: Synthetic construct

<400> SEQUENCE: 54
gauaggccau uugcagaca 19

<210> SEQ ID NO 55
<211> LENGTH: 19
<212> TYPE: DNA
<213> ORGANISM: Artificial
<220> FEATURE:
<223> OTHER INFORMATION: Synthetic construct

<400> SEQUENCE: 55
gauaugagac uuucuacuc 19

<210> SEQ ID NO 56
<211> LENGTH: 19
<212> TYPE: DNA
<213> ORGANISM: Artificial
<220> FEATURE:
<223> OTHER INFORMATION: Synthetic construct

<400> SEQUENCE: 56
gauguuggcu uuucuggau 19

<210> SEQ ID NO 57
<211> LENGTH: 19
<212> TYPE: DNA
<213> ORGANISM: Artificial
<220> FEATURE:
<223> OTHER INFORMATION: Synthetic construct

<400> SEQUENCE: 57
gauucuuagu cauacuuga 19

<210> SEQ ID NO 58
<211> LENGTH: 19
<212> TYPE: DNA
<213> ORGANISM: Artificial
<220> FEATURE:
<223> OTHER INFORMATION: Synthetic construct

<400> SEQUENCE: 58
gcaacguggu acuacuuuu 19

<210> SEQ ID NO 59
<211> LENGTH: 19
<212> TYPE: DNA
<213> ORGANISM: Artificial
<220> FEATURE:
<223> OTHER INFORMATION: Synthetic construct

<400> SEQUENCE: 59
gcaagaugcu ccgcaagga 19

-continued

<210> SEQ ID NO 60
<211> LENGTH: 19
<212> TYPE: DNA
<213> ORGANISM: Artificial
<220> FEATURE:
<223> OTHER INFORMATION: Synthetic construct

<400> SEQUENCE: 60
gcacaauuuc caccuuauu 19

<210> SEQ ID NO 61
<211> LENGTH: 19
<212> TYPE: DNA
<213> ORGANISM: Artificial
<220> FEATURE:
<223> OTHER INFORMATION: Synthetic construct

<400> SEQUENCE: 61
gcagaagccc uguggcaac 19

<210> SEQ ID NO 62
<211> LENGTH: 19
<212> TYPE: DNA
<213> ORGANISM: Artificial
<220> FEATURE:
<223> OTHER INFORMATION: Synthetic construct

<400> SEQUENCE: 62
gcagcaacgu gggagaaag 19

<210> SEQ ID NO 63
<211> LENGTH: 19
<212> TYPE: DNA
<213> ORGANISM: Artificial
<220> FEATURE:
<223> OTHER INFORMATION: Synthetic construct

<400> SEQUENCE: 63
gcagcaggcu cuucacuga 19

<210> SEQ ID NO 64
<211> LENGTH: 19
<212> TYPE: DNA
<213> ORGANISM: Artificial
<220> FEATURE:
<223> OTHER INFORMATION: Synthetic construct

<400> SEQUENCE: 64
gcaggcucuu cacugauag 19

<210> SEQ ID NO 65
<211> LENGTH: 19
<212> TYPE: DNA
<213> ORGANISM: Artificial
<220> FEATURE:
<223> OTHER INFORMATION: Synthetic construct

<400> SEQUENCE: 65
gcaguuauga agccaauuc 19

<210> SEQ ID NO 66
<211> LENGTH: 19
<212> TYPE: DNA
<213> ORGANISM: Artificial
<220> FEATURE:
<223> OTHER INFORMATION: Synthetic construct

<210> SEQ ID NO 66

<400> SEQUENCE: 66
gcaugaccca ccuacacua          19

<210> SEQ ID NO 67
<211> LENGTH: 19
<212> TYPE: DNA
<213> ORGANISM: Artificial
<220> FEATURE:
<223> OTHER INFORMATION: Synthetic construct

<400> SEQUENCE: 67
gccauggguu cuucacuga          19

<210> SEQ ID NO 68
<211> LENGTH: 19
<212> TYPE: DNA
<213> ORGANISM: Artificial
<220> FEATURE:
<223> OTHER INFORMATION: Synthetic construct

<400> SEQUENCE: 68
gcggcucgcu caacgucaa          19

<210> SEQ ID NO 69
<211> LENGTH: 19
<212> TYPE: DNA
<213> ORGANISM: Artificial
<220> FEATURE:
<223> OTHER INFORMATION: Synthetic construct

<400> SEQUENCE: 69
gcgggucuac uuccucaaa          19

<210> SEQ ID NO 70
<211> LENGTH: 19
<212> TYPE: DNA
<213> ORGANISM: Artificial
<220> FEATURE:
<223> OTHER INFORMATION: Synthetic construct

<400> SEQUENCE: 70
gcuacaggcc agcuuauga          19

<210> SEQ ID NO 71
<211> LENGTH: 19
<212> TYPE: DNA
<213> ORGANISM: Artificial
<220> FEATURE:
<223> OTHER INFORMATION: Synthetic construct

<400> SEQUENCE: 71
gcugaucacc gucuaguug          19

<210> SEQ ID NO 72
<211> LENGTH: 19
<212> TYPE: DNA
<213> ORGANISM: Artificial
<220> FEATURE:
<223> OTHER INFORMATION: Synthetic construct

<400> SEQUENCE: 72
ggaagugccu accaugcau          19

<210> SEQ ID NO 73
<211> LENGTH: 19

<212> TYPE: DNA
<213> ORGANISM: Artificial
<220> FEATURE:
<223> OTHER INFORMATION: Synthetic construct

<400> SEQUENCE: 73
ggagaaaagg caguuauga 19

<210> SEQ ID NO 74
<211> LENGTH: 19
<212> TYPE: DNA
<213> ORGANISM: Artificial
<220> FEATURE:
<223> OTHER INFORMATION: Synthetic construct

<400> SEQUENCE: 74
ggagcauggu cucgcccaa 19

<210> SEQ ID NO 75
<211> LENGTH: 19
<212> TYPE: DNA
<213> ORGANISM: Artificial
<220> FEATURE:
<223> OTHER INFORMATION: Synthetic construct

<400> SEQUENCE: 75
ggaggcagca ggcucuuca 19

<210> SEQ ID NO 76
<211> LENGTH: 19
<212> TYPE: DNA
<213> ORGANISM: Artificial
<220> FEATURE:
<223> OTHER INFORMATION: Synthetic construct

<400> SEQUENCE: 76
ggccuucgau uacaucaag 19

<210> SEQ ID NO 77
<211> LENGTH: 19
<212> TYPE: DNA
<213> ORGANISM: Artificial
<220> FEATURE:
<223> OTHER INFORMATION: Synthetic construct

<400> SEQUENCE: 77
ggggaaaagg caauaauuu 19

<210> SEQ ID NO 78
<211> LENGTH: 19
<212> TYPE: DNA
<213> ORGANISM: Artificial
<220> FEATURE:
<223> OTHER INFORMATION: Synthetic construct

<400> SEQUENCE: 78
gguagguucu cgggacuga 19

<210> SEQ ID NO 79
<211> LENGTH: 19
<212> TYPE: DNA
<213> ORGANISM: Artificial
<220> FEATURE:
<223> OTHER INFORMATION: Synthetic construct

<400> SEQUENCE: 79

-continued guagauucca ggaggagaa 19

<210> SEQ ID NO 80
<211> LENGTH: 19
<212> TYPE: DNA
<213> ORGANISM: Artificial
<220> FEATURE:
<223> OTHER INFORMATION: Synthetic construct

<400> SEQUENCE: 80
guagcaagau guuggcuuu 19

<210> SEQ ID NO 81
<211> LENGTH: 19
<212> TYPE: DNA
<213> ORGANISM: Artificial
<220> FEATURE:
<223> OTHER INFORMATION: Synthetic construct

<400> SEQUENCE: 81
guagggacau gaucagcau 19

<210> SEQ ID NO 82
<211> LENGTH: 19
<212> TYPE: DNA
<213> ORGANISM: Artificial
<220> FEATURE:
<223> OTHER INFORMATION: Synthetic construct

<400> SEQUENCE: 82
guaguugguu gaaguagca 19

<210> SEQ ID NO 83
<211> LENGTH: 19
<212> TYPE: DNA
<213> ORGANISM: Artificial
<220> FEATURE:
<223> OTHER INFORMATION: Synthetic construct

<400> SEQUENCE: 83
guucuucacu gaccuugga 19

<210> SEQ ID NO 84
<211> LENGTH: 19
<212> TYPE: DNA
<213> ORGANISM: Artificial
<220> FEATURE:
<223> OTHER INFORMATION: Synthetic construct

<400> SEQUENCE: 84
uaaaacccau uucacaaga 19

<210> SEQ ID NO 85
<211> LENGTH: 19
<212> TYPE: DNA
<213> ORGANISM: Artificial
<220> FEATURE:
<223> OTHER INFORMATION: Synthetic construct

<400> SEQUENCE: 85
uaaaacccau uucacaaga 19

<210> SEQ ID NO 86
<211> LENGTH: 19
<212> TYPE: DNA
<213> ORGANISM: Artificial

<220> FEATURE:
<223> OTHER INFORMATION: Synthetic construct

<400> SEQUENCE: 86
uaagacccgu gugaaugug 19

<210> SEQ ID NO 87
<211> LENGTH: 19
<212> TYPE: DNA
<213> ORGANISM: Artificial
<220> FEATURE:
<223> OTHER INFORMATION: Synthetic construct

<400> SEQUENCE: 87
uaagacucau ggacauuuc 19

<210> SEQ ID NO 88
<211> LENGTH: 19
<212> TYPE: DNA
<213> ORGANISM: Artificial
<220> FEATURE:
<223> OTHER INFORMATION: Synthetic construct

<400> SEQUENCE: 88
uacuugaacu ugucucauu 19

<210> SEQ ID NO 89
<211> LENGTH: 19
<212> TYPE: DNA
<213> ORGANISM: Artificial
<220> FEATURE:
<223> OTHER INFORMATION: Synthetic construct

<400> SEQUENCE: 89
uagacuucau ugacugugu 19

<210> SEQ ID NO 90
<211> LENGTH: 19
<212> TYPE: DNA
<213> ORGANISM: Artificial
<220> FEATURE:
<223> OTHER INFORMATION: Synthetic construct

<400> SEQUENCE: 90
uagcucccac uuucaagaa 19

<210> SEQ ID NO 91
<211> LENGTH: 19
<212> TYPE: DNA
<213> ORGANISM: Artificial
<220> FEATURE:
<223> OTHER INFORMATION: Synthetic construct

<400> SEQUENCE: 91
ucaagcauaa gccaauaaa 19

<210> SEQ ID NO 92
<211> LENGTH: 19
<212> TYPE: DNA
<213> ORGANISM: Artificial
<220> FEATURE:
<223> OTHER INFORMATION: Synthetic construct

<400> SEQUENCE: 92
ucacaagaga agauugaga 19

<210> SEQ ID NO 93
<211> LENGTH: 19
<212> TYPE: DNA
<213> ORGANISM: Artificial
<220> FEATURE:
<223> OTHER INFORMATION: Synthetic construct

<400> SEQUENCE: 93
ucaccaggcu ugcaaauga 19

<210> SEQ ID NO 94
<211> LENGTH: 19
<212> TYPE: DNA
<213> ORGANISM: Artificial
<220> FEATURE:
<223> OTHER INFORMATION: Synthetic construct

<400> SEQUENCE: 94
ucacugaccu uggacuuug 19

<210> SEQ ID NO 95
<211> LENGTH: 19
<212> TYPE: DNA
<213> ORGANISM: Artificial
<220> FEATURE:
<223> OTHER INFORMATION: Synthetic construct

<400> SEQUENCE: 95
ucauaccugu gcaauacug 19

<210> SEQ ID NO 96
<211> LENGTH: 19
<212> TYPE: DNA
<213> ORGANISM: Artificial
<220> FEATURE:
<223> OTHER INFORMATION: Synthetic construct

<400> SEQUENCE: 96
ucuaagaccc gugugaaug 19

<210> SEQ ID NO 97
<211> LENGTH: 19
<212> TYPE: DNA
<213> ORGANISM: Artificial
<220> FEATURE:
<223> OTHER INFORMATION: Synthetic construct

<400> SEQUENCE: 97
ucucagagcu cagcagaag 19

<210> SEQ ID NO 98
<211> LENGTH: 19
<212> TYPE: DNA
<213> ORGANISM: Artificial
<220> FEATURE:
<223> OTHER INFORMATION: Synthetic construct

<400> SEQUENCE: 98
ugacauuagc ucccacuuu 19

<210> SEQ ID NO 99
<211> LENGTH: 19
<212> TYPE: DNA
<213> ORGANISM: Artificial
<220> FEATURE:
<223> OTHER INFORMATION: Synthetic construct

<400> SEQUENCE: 99
ugaccagggu ggcccaguu 19

<210> SEQ ID NO 100
<211> LENGTH: 19
<212> TYPE: DNA
<213> ORGANISM: Artificial
<220> FEATURE:
<223> OTHER INFORMATION: Synthetic construct

<400> SEQUENCE: 100
ugacccaccu acacuacaa 19

<210> SEQ ID NO 101
<211> LENGTH: 19
<212> TYPE: DNA
<213> ORGANISM: Artificial
<220> FEATURE:
<223> OTHER INFORMATION: Synthetic construct

<400> SEQUENCE: 101
ugagguaguu gguugaagu 19

<210> SEQ ID NO 102
<211> LENGTH: 19
<212> TYPE: DNA
<213> ORGANISM: Artificial
<220> FEATURE:
<223> OTHER INFORMATION: Synthetic construct

<400> SEQUENCE: 102
uggcuuaccu uaugaagac 19

<210> SEQ ID NO 103
<211> LENGTH: 19
<212> TYPE: DNA
<213> ORGANISM: Artificial
<220> FEATURE:
<223> OTHER INFORMATION: Synthetic construct

<400> SEQUENCE: 103
ugggccagcu ccugcagua 19

<210> SEQ ID NO 104
<211> LENGTH: 19
<212> TYPE: DNA
<213> ORGANISM: Artificial
<220> FEATURE:
<223> OTHER INFORMATION: Synthetic construct

<400> SEQUENCE: 104
uuaagacuca uggacauuu 19

<210> SEQ ID NO 105
<211> LENGTH: 19
<212> TYPE: DNA
<213> ORGANISM: Artificial
<220> FEATURE:
<223> OTHER INFORMATION: Synthetic construct

<400> SEQUENCE: 105
uuaugaagac caagcaguu 19

<210> SEQ ID NO 106

<211> LENGTH: 19
<212> TYPE: DNA
<213> ORGANISM: Artificial
<220> FEATURE:
<223> OTHER INFORMATION: Synthetic construct

<400> SEQUENCE: 106
uucaaugucu gucucuguu 19

<210> SEQ ID NO 107
<211> LENGTH: 19
<212> TYPE: DNA
<213> ORGANISM: Artificial
<220> FEATURE:
<223> OTHER INFORMATION: Synthetic construct

<400> SEQUENCE: 107
uuucaagcau aagccaaua 19

<210> SEQ ID NO 108
<211> LENGTH: 19
<212> TYPE: DNA
<213> ORGANISM: Artificial
<220> FEATURE:
<223> OTHER INFORMATION: Synthetic construct

<400> SEQUENCE: 108
uuucauaccu gugcaauac 19

<210> SEQ ID NO 109
<211> LENGTH: 19
<212> TYPE: DNA
<213> ORGANISM: Artificial
<220> FEATURE:
<223> OTHER INFORMATION: Synthetic construct

<400> SEQUENCE: 109
uuugaacccu gaaauguug 19

<210> SEQ ID NO 110
<211> LENGTH: 19
<212> TYPE: DNA
<213> ORGANISM: Artificial
<220> FEATURE:
<223> OTHER INFORMATION: Synthetic construct

<400> SEQUENCE: 110
uuugaaggaa gcacaauuu 19

<210> SEQ ID NO 111
<211> LENGTH: 21
<212> TYPE: DNA
<213> ORGANISM: Artificial
<220> FEATURE:
<223> OTHER INFORMATION: Synthetic construct

<400> SEQUENCE: 111
gcauggcuua ccuuaugaat t 21

<210> SEQ ID NO 112
<211> LENGTH: 21
<212> TYPE: DNA
<213> ORGANISM: Artificial
<220> FEATURE:
<223> OTHER INFORMATION: Synthetic construct

<400> SEQUENCE: 112
uucauaaggu aagccaugct t 21

<210> SEQ ID NO 113
<211> LENGTH: 21
<212> TYPE: DNA
<213> ORGANISM: Artificial
<220> FEATURE:
<223> OTHER INFORMATION: Synthetic construct

<400> SEQUENCE: 113
cgucuaguug ggaaaguaat t 21

<210> SEQ ID NO 114
<211> LENGTH: 21
<212> TYPE: DNA
<213> ORGANISM: Artificial
<220> FEATURE:
<223> OTHER INFORMATION: Synthetic construct

<400> SEQUENCE: 114
uuacuuuccc aacuagacgt t 21

<210> SEQ ID NO 115
<211> LENGTH: 21
<212> TYPE: DNA
<213> ORGANISM: Artificial
<220> FEATURE:
<223> OTHER INFORMATION: Synthetic construct

<400> SEQUENCE: 115
guagcaagau guuggcuuut t 21

<210> SEQ ID NO 116
<211> LENGTH: 21
<212> TYPE: DNA
<213> ORGANISM: Artificial
<220> FEATURE:
<223> OTHER INFORMATION: Synthetic construct

<400> SEQUENCE: 116
aaagccaaca ucuugcuact t 21

<210> SEQ ID NO 117
<211> LENGTH: 21
<212> TYPE: DNA
<213> ORGANISM: Artificial
<220> FEATURE:
<223> OTHER INFORMATION: Synthetic construct

<400> SEQUENCE: 117
gcauggcuua ccucaugaat t 21

<210> SEQ ID NO 118
<211> LENGTH: 21
<212> TYPE: DNA
<213> ORGANISM: Artificial
<220> FEATURE:
<223> OTHER INFORMATION: Synthetic construct

<400> SEQUENCE: 118
uucaugaggu aagccaugct t 21

<210> SEQ ID NO 119
<211> LENGTH: 21
<212> TYPE: DNA

-continued

```
<213> ORGANISM: Artificial
<220> FEATURE:
<223> OTHER INFORMATION: Synthetic construct

<400> SEQUENCE: 119

gacagcuccu ucaguaugat t                                                21


<210> SEQ ID NO 120
<211> LENGTH: 21
<212> TYPE: DNA
<213> ORGANISM: Artificial
<220> FEATURE:
<223> OTHER INFORMATION: Synthetic construct

<400> SEQUENCE: 120

ucauacugaa ggagcuguct t                                                21
```

INDUCING PROLIFERATION OF CARDIOMYOCYTES AND THERAPEUTIC USES RELATED THERETO

CROSS-REFERENCE TO RELATED APPLICATIONS

This application is the National Stage of International Application No. PCT/US2019/046566 filed Aug. 14, 2019, which claims the benefit of U.S. Provisional Application No. 62/718,583 filed Aug. 14, 2018 and U.S. Provisional Application No. 62/813,467 filed Mar. 4, 2019. The entirety of each of these applications is hereby incorporated by reference for all purposes.

STATEMENT REGARDING FEDERALLY SPONSORED RESEARCH OR DEVELOPMENT

This invention was made with government support under HL127726 awarded by the National Institutes of Health. The government has certain rights in the invention.

INCORPORATION-BY-REFERENCE OF MATERIAL SUBMITTED AS A TEXT FILE VIA THE OFFICE ELECTRONIC FILING SYSTEM EFS-WEB

The Sequence Listing associated with this application is provided in text format in lieu of a paper copy, and is hereby incorporated by reference into the specification. The name of the text file containing the Sequence Listing is 18222PCT_ST25.txt. The text file is 22 KB, was created on Aug. 14, 2019, and is being submitted electronically via EFSWeb.

BACKGROUND

Human hearts are typically unable to regenerate cardiac tissue following traumatic injury leading to heart failure. Thus, there is a need to identify methods of improving cardiac regeneration. Compared to low oxygen environment of the fetus, the oxygen-rich postnatal environment at birth induces physiological changes. Cardiomyocytes in the heart dramatically decrease spontaneous replication several weeks after birth. Nakada et al. report oxygen-dependent mitochondrial metabolism is a major driver of cell cycle arrest of cardiomyocytes. Nature, 2017, 541(7636):222-227. Thyroid hormone increases aerobic metabolism, induces mitochondrial biogenesis and activates oxidative phosphorylation (OXPHOS), a major source of ROS, in the early postnatal period. Li et al. Stem Cell Res. 2014, 13 (3 Pt B): 582-91.

The human heart contains a mixture of mononuclear and binuclear cardiomyocytes. Binuclear cardiomyocytes are believed to be more actively involved in cardiomyocyte replication and regeneration. Naqvi et al. report a thyroid hormone surge activates the IGF-1/IGF1-R/Akt pathway after birth and initiates a brief but intense proliferative burst of predominantly binuclear cardiomyocytes. Cell. 2014, 157(4): 795-807.

Molina el al report zebrafish chemical screening reveals an inhibitor of DUSP6 that expands cardiac cell lineages. Nat. Chem. Biol. 2009, 5:680-687

Ueda et al. report dual-specificity phosphatase 5 (DUSP5) as a direct transcriptional target of tumor suppressor p53. Oncogene. 2003, 22(36):5586-91.

US Published Patent Application 2018/0000778 (Ramchandran et al.) reports small molecule antagonists of DUSP5. See also US 2007/0276135 (Khvorova et al.).

References cited herein are not an admission of prior art.

SUMMARY

This disclosure relates to methods of treating or preventing heart malformations or cardiovascular diseases comprising administering an effective amount of thyroid hormone in combination with i) an agent that decreases DUSP5 and/or DUSP6 expression and/or ii) a beta-adrenergic blocking agent to a subject in need thereof. In certain embodiments, this disclosure relates to in vivo and in vitro methods of inducing proliferation of cardiomyocytes using agents or combinations of agents disclosed herein.

In certain embodiments, this disclosure relates to methods of treating or preventing heart malformation or cardiovascular disease comprising administering an effective amount of thyroid hormone in combination with a beta-adrenergic blocking agent to a subject in need thereof. In certain embodiments, this disclosure relates to methods of inducing proliferation of cardiomyocytes comprising administering an effective amount of a DUSP5 and/or DUSP6 inhibitor to a subject.

In certain embodiments, the beta-adrenergic blocking agent is selected from acebutolol, atenolol, betaxolol, bisoprolol, carteolol, carvedilol, esmolol, labetalol, metoprolol, nadolol, nebivolol, penbutolol, pindolol, propranolol, sotalol, timolol, or salts thereof. In certain embodiments, the beta-adrenergic blocking agent is administered in combination with a mitogen. In certain embodiments, the mitogen is neuregulin, IGF-1, YAP1, ERBB2.

In certain embodiments, the cardiovascular disease is selected from coronary artery disease, heart failure, cardiomyopathy, heart valve disease, and cardiac arrhythmias. In certain embodiments, the subject is diagnosed with a heart attack, angina, or stroke, diabetes, angina pectoris due to coronary atherosclerosis, hypertension, migraine headaches, glaucoma, hyperthyroidism, fibromyalgia, generalized anxiety disorder, parkinsonian tremor, and atrial fibrillation.

In certain embodiments, this disclosure relates to methods of inducing proliferation of cardiomyocytes comprising administering an effective amount of thyroid hormone in combination with a beta-adrenergic blocking agent to a subject in need thereof. In certain embodiments, the beta-adrenergic blocking agent is siRNA. In certain embodiments, the combination is administered is administered to a newborn within 1 to 7 days of birth. In certain embodiments, the combination is administered to a newborn within 8 to 14 days of birth. In certain embodiments, the combination is administered to a newborn within 15 to 21 days of birth. In certain embodiments, the combination is administered to a subject more than 21 days after birth.

In certain embodiments, the combination is administered by intravenous (IV) injection, direct injection into the cardiac tissue, direct injection into apical cardiac tissue, or pericardial cavity. In certain embodiments, the combination is administered to a subject at risk of, exhibiting symptoms of, or diagnosed with a cardiovascular disease, condition, or injury. In certain embodiments, the combination is administered to a subject at risk of, exhibiting symptoms of, or diagnosed with heart disease, heart attack, stroke, heart failure, arrhythmia, heart valve disease, congenital heart defect, patent ductus arteriosus, ventricular septal defect, truncus arteriosus, atrioventricular septal defect, tetralogy of Fallot, transposition of the great arteries, hypoplastic left heart syndrome, tricuspid atresia, or heart murmur, for use in the treatment or prevention thereof.

In certain embodiments, this disclosure relates to an in vitro method of inducing proliferation of cardiomyocytes comprising administering an effective amount of a thyroid hormone in combination with a beta-adrenergic blocking agent to a cardiac cell.

In certain embodiments, this disclosure relates to an in vitro method of inducing proliferation of cardiomyocytes comprising administering an effective amount of a thyroid hormone in combination with a DUSP5 or DUSP6 inhibitor to a cardiac cell.

In certain embodiments, this disclosure relates to methods of inducing proliferation of cardiomyocytes comprising administering an effective amount of a DUSP5 and/or DUSP6 inhibitor to a subject, wherein the DUSP5 or DUSP6 inhibitor is a small molecule or wherein the DUSP5 or DUSP6 inhibitor is a polysulfonated aromatic compound with a carbazole or naphthalene scaffold.

In certain embodiments, the DUSP5 or DUSP6 inhibitor is a compound selected from 2-benzylidene-3-(cyclohexylamino)-2,3-dihydro-1H-inden-1-one (BCI), carbazole-1,3,6-trisulfonic acid, carbazole-1,3,6,8-tetrasulfonic acid, 8-hydroxynaphthalene-1,6-disulfonic acid (RR527), 8-amino-4-hydroxynaphthalene-2-sulfonic acid (RR535), 8,8'-(diazene-1,2-diyl)bis(4-hydroxy naphthalene-2-sulfonic acid) (RR601), $1^2,3^2,5^2,7^2$-tetrahydroxy-1,3,5,7(1,3)-tetrabenzene cyclooctaphane-$1^5,3^5,5^5,7^5$-tetrasulfonic acid (RR701), derivatives, prodrugs, alkylesters, or alternative salts thereof.

In certain embodiments, the DUSP5 or DUSP6 inhibitor is siRNA or an antisense therapy.

In certain embodiments, the DUSP5 or DUSP6 inhibitor is siRNA comprising a sense region and an antisense region, wherein said sense region and said antisense region together form a duplex region, said antisense region and said sense region are each 18-30 nucleotides in length and said antisense region comprises a sequence a sequence selected from the group consisting of SEQ ID Nos: 1-120 or variant thereof.

In certain embodiments, the DUSP5 or DUSP6 inhibitor is administered to a newborn within 1 to 7 days of birth.

In certain embodiments, the DUSP5 or DUSP6 inhibitor is administered to a newborn within 8 to 14 days of birth. In certain embodiments, the DUSP5 or DUSP6 inhibitor is administered to a newborn within 15 to 21 days of birth. In certain embodiments, the DUSP5 or DUSP6 inhibitor is administered to a subject more than 21 days after birth In certain embodiments, the DUSP5 or DUSP6 inhibitor is administered by intravenous (IV) injection, direct injection into the cardiac tissue, direct injection into apical cardiac tissue, or pericardial cavity.

In certain embodiments, the DUSP5 or DUSP6 inhibitor is administered at risk of, exhibiting symptoms of, or diagnosed with a cardiovascular disease, condition, or injury. In certain embodiments, the DUSP5 or DUSP6 inhibitor is administered at risk of, exhibiting symptoms of, or diagnosed with heart disease, heart attack, stroke, heart failure, arrhythmia, heart valve disease, congenital heart defect, patent ductus arteriosus, ventricular septal defect, truncus arteriosus, atrioventricular septal defect, tetralogy of Fallot, transposition of the great arteries, hypoplastic left heart syndrome, tricuspid atresia, or heart murmur, for use in the treatment or prevention thereof.

In certain embodiments, this disclosure relates to an in vitro method of inducing proliferation of cardiomyocytes comprising administering an effective amount of a DUSP5 and/or DUSP6 inhibitor to a cardiac cell.

DETAILED DISCUSSION

Figure 1A:
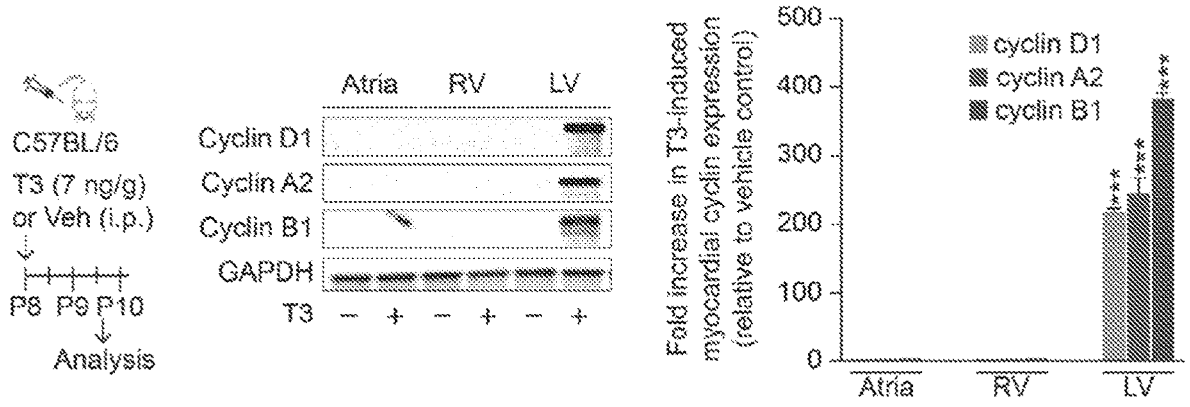
FIG. 1A shows data indicating developmental loss of $T_3$-induced proliferative signaling in postnatal cardiomyocytes.
Figure 1B:
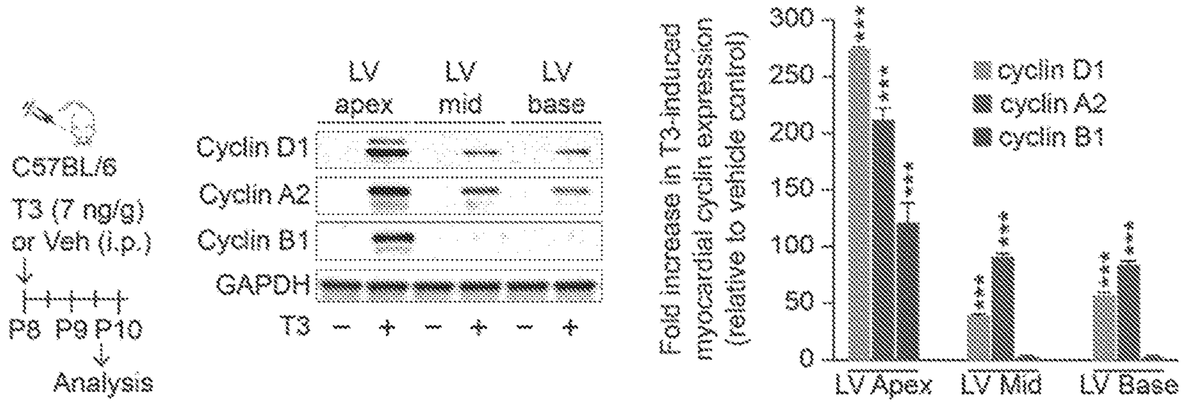
FIG. 1B shows data indicating an effect of in vivo $T_3$ treatment on regional cyclin D1, A2, and B1 expression in the post-neonatal heart.

Before the present disclosure is described in greater detail, it is to be understood that this disclosure is not limited to embodiments described, and as such may, of course, vary. It is also to be understood that the terminology used herein is for describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

As used in this disclosure and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") have the meaning ascribed to them in U.S. patent law in that they are inclusive or open-ended and do not exclude additional, unrecited elements or method steps. The term "comprising" in reference to an oligonucleotide having a nucleic acid sequence refers to an oligonucleotide that may contain additional 5' (5' terminal end) or 3' (3' terminal end) nucleotides, i.e., the term is intended to include the oligonucleotide sequence within a larger nucleic acid. "Consisting essentially of" or "consists of" or the like, when applied to methods and compositions encompassed by the present disclosure refers to compositions like those disclosed herein that exclude certain prior art elements to provide an inventive feature of a claim, but which may contain additional composition components or method steps, etc., that do not materially affect the basic and novel characteristic(s) of the compositions or methods, compared to those of the corresponding compositions or methods disclosed herein. The term "consisting of" in reference to an oligonucleotide having a nucleotide sequence refers an oligonucleotide having the exact number of nucleotides in the sequence and not more or having not more than a range of nucleotide expressly specified in the claim. For example, "5" sequence consisting of is limited only to the 5' end, i.e., the 3' end may contain additional nucleotides. Similarly, a "3" sequence consisting of is limited only to the 3' end, and the 5' end may contain additional nucleotides.

The following abbreviations and acronyms are used: β1-AR (β1-adrenergic receptor), CM (cardiomyocyte), DUSP5 (dual specificity phosphatase 5), EdU (5-ethynyl-2'-deoxyuridine), EF (ejection fraction), ERK1/2 (extracellular signal-regulated kinase-1/2), FS (fractional shortening), FWd (left ventricle free wall dimension at diastole), FWs (left ventricle free wall dimension at systole), IGF-1 (insulin-like growth factor-1), IGF-1R (insulin-like growth factor-1 receptor), IVSd (intraventricular septum dimension at diastole), IVSs (intraventricular septum dimension at systole), LV (left ventricle), LVEDD (left ventricle end-diastolic dimension), LVESD (left ventricle end-systolic dimension), MAPK (mitogen-activated protein kinase), MEK (mitogen-activated protein kinase kinase), P (postnatal day), pH3 (phospho-histone H3), RV (right ventricle).

As sued herein, the terms "$T_3$" and "thyroid hormone" refer to the compound, 3,3',5-triiodo-L-thyronine, IUPAC name (2S)-2-amino-3-[4-(4-hydroxy-3-iodophenoxy)-3,5-diiodophenyl]propanoic acid and salts thereof. $T_3$ derivatives are contemplated as a substitution of $T_3$ for uses in all methods and compositions disclosed herein. Example derivatives include tyrosine substituted with one or more iodine and deaminated or decarboxylated derivatives such as, thyroxine ($T_4$), 3,3',5'-triiodothyronine ($rT_3$), diiodothyronine ($T_2$), monoiodothyronine ($T_1$), 3,5,3'-triiodothyroacetic acid (Triac), 3,3',5,5'-tetraiodoacetic acid (Tetrac), 3,5,3'-triiodothyropropionic acid, 3-iodo-thyroacetic acid, 3,3',5-triiodothyronamine (Triam), 3,5-diiodo-thyronamine ($T_2$AM), 3-iodothyronamine (3-$T_1$AM), thyronamine ($T_0$AM), prodrugs, carboxylic acid esters, and salts thereof.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing an oxygen atom with a sulfur atom or replacing an amino group with a hydroxyl group. The derivative may be a prodrug. Derivatives may be prepared by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

The term "substituted" refers to a molecule wherein at least one hydrogen atom is replaced with a substituent. When substituted, one or more of the groups are "substituents." The molecule may be multiply substituted. In the case of an oxo substituent ("═O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —$NR_aR_b$, —$NR_aC$(═O)$R_b$, —$NR_aC$(═O)$NR_aNR_b$, —$NR_aC$(═O)$OR_b$, —$NR_aSO_{2Rb}$, —C(═O)$R_a$, —C(═O)$OR_a$, —C(═O)$NR_aR_b$, —OC(═O)$NR_aR_b$, —ORa, —SRa, —SORa, —S(═O)$_2$Ra, —OS(═O)$_2$Ra and —S(═O)$_2$$OR_a$. $R_a$ and $R_b$ in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, and heteroarylalkyl.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Typical prodrugs are pharmaceutically acceptable esters. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like.

For example, if a disclosed compound or a pharmaceutically acceptable form of the compound contains a carboxylic acid functional group, a prodrug can comprise a pharmaceutically acceptable ester formed by the replacement of the hydrogen atom of the acid group with a group such as ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as beta-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl.

If a disclosed compound or a pharmaceutically acceptable form of the compound contains an alcohol functional group, a prodrug can be formed by the replacement of the hydrogen atom of the alcohol group with a group such as ($C_1$-$C_6$)alkanoyloxymethyl, 1-(($C_1$-$C_6$)alkanoyloxy) ethyl, 1-methyl-1(($C_1$-$C_6$)alkanoyloxy)ethyl ($C_1$-$C_6$)alkoxycarbonyloxymethyl, —N—(C1-C6)alkoxycarbonylaminomethyl, succinoyl, ($C_1$-$C_6$)alkanoyl, alpha-amino($C_1$-$C_4$)alkanoyl, arylacyl and alpha-aminoacyl, or alpha-aminoacyl-alpha-aminoacyl, where each alpha-aminoacyl group is independently selected from naturally occurring L-amino acids P(O)(OH)$_2$, —P(O)(O(C1-$C_6$)alkyl)$_2$, and glycosyl (the radical resulting from the removal of a hydroxyl group of the hemiacetal form of a carbohydrate).

If a disclosed compound or a pharmaceutically acceptable form of the compound incorporates an amine functional group, a prodrug can be formed by the replacement of a hydrogen atom in the amine group with a group such as R-carbonyl, RO-carbonyl, NRR'-carbonyl where R and R' are each independently ($C_1$-$C_{10}$)alkyl, ($C_3$-$C_7$)cycloalkyl, benzyl, a natural alpha-aminoacyl, —C(OH)C(O)O$Y^1$ wherein $Y^1$ is H, ($C_1$-$C_6$)alkyl or benzyl, —C(O$Y^2$)$Y^3$ wherein $Y^2$ is ($C_1$-$C_4$) alkyl and $Y^3$ is ($C_1$-$C_6$)alkyl, carboxy ($C_1$-$C_6$)alkyl, amino($C_1$-$C_4$)alkyl or mono-N or di-N,N—($C_1$-$C_6$)alkylaminoalkyl, —C($Y^4$)$Y^5$ wherein $Y^4$ is H or methyl and $Y^5$ is mono-N— or di-N,N—($C_1$-$C_6$)alkylamino, morpholino, piperidin-1-yl or pyrrolidin-1-yl.

As used herein, "pharmaceutically acceptable esters" include, but are not limited to, alkyl, alkenyl, alkynyl, aryl, arylalkyl, and cycloalkyl esters of acidic groups, including, but not limited to, carboxylic acids, phosphoric acids, phosphinic acids, sulfonic acids, sulfinic acids, and boronic acids.

As used herein, "pharmaceutically acceptable enol ethers" include, but are not limited to, derivatives of formula —C═C(OR) where R can be selected from alkyl, alkenyl, alkynyl, aryl, aralkyl, and cycloalkyl. Pharmaceutically acceptable enol esters include, but are not limited to, derivatives of formula —C═C(OC(O)R) where R can be selected from hydrogen, alkyl, alkenyl, alkynyl, aryl, aralkyl, and cycloalkyl.

The term "patient" and "subject" are interchangeable and may be taken to mean any living organism which may be treated with compounds of the present disclosure. As such, the terms "patient" and "subject" may include, but is not limited to, any non-human mammal, primate or human. In some embodiments, the "patient" or "subject" is a mammal, such as mice, rats, other rodents, rabbits, dogs, cats, swine, cattle, sheep, horses, primates, or humans. In some embodiments, the patient or subject is an adult, child or infant. In some embodiments, the patient or subject is a human.

As used herein, the terms "treat" and "treating" are not limited to the case where the subject (e.g. patient) is cured and the disease is eradicated. Rather, embodiments of the present disclosure also contemplate treatment that merely reduces symptoms, and/or delays disease progression.

As used herein, "pharmaceutical formulation" and "pharmaceutical composition" can be used interchangeably. The composition may be administered to patients in an amount effective, especially to enhance pharmacological response in an animal or human organism. As used herein, the term "effective amount" refers to an amount sufficient to realize a desired biological effect. The appropriate dosage may vary depending upon known factors such as the pharmacodynamic characteristics of the particular active agent, age, health, and weight of the host organism; the condition(s) to be treated, nature and extent of symptoms, kind of concurrent treatment, frequency of treatment, the need for prevention or therapy and/or the effect desired. The dosage will also be calculated dependent upon the particular route of administration selected. Further refinement of the calculations necessary to determine the appropriate dosage for treatment is routinely made by a practitioner, in the light of the relevant circumstances. The titer may be determined by conventional techniques.

Methods of Use

The issue of how and when cardiomyocytes lose their ability to divide has captured the attention of specialists interested in cardiovascular biology. These endeavors have impacted diverse fields such as regenerative repair of the heart, and congenital heart conditions in which the postnatal cardiomyocyte endowment is diminished by disease. There is considerable debate as to when postnatal cardiomyocytes lose proliferative capacity. The consensus view is that in mice it occurs by the end of the neonatal period (by postnatal day 6), and involves all ventricular cardiomyocytes (Tzahor et al., Science 356, 1035, 2017).

Experimental evidence indicates that in cardiac muscle cells it occurs gradually, extending from the base of the left ventricle to its apex, over postnatal days-7-15, and loss of proliferative capacity is caused by the post-neonatal expression of DUSP5, a nuclear p-ERK1/2-specific phosphatase that prevents sustained ERK1/2 activation in the nucleus (this activation is a prerequisite for proliferative signaling by all growth factors). DUSP5 expression not only initiates loss of proliferative capacity but it also maintains it. This latter finding suggests a strategy to reversibly activate proliferative competence in adult cardiac muscle cells.

Experimental evidence also indicates that cardiomyocyte DUSP5 expression is caused by sympathetic βi-adrenergic receptor activation. This discovery offers immediate solutions for regenerative therapies. Because many $\beta_1$-selective antagonists are used clinically, it may be possible to engage in cardiac regenerative therapies.

In certain embodiments, this disclosure relates to in vivo and in vitro methods of inducing proliferation of cardiomyocytes by administering or mixing an agent or combination of agents disclosed herein and uses in managing diseases and conditions relates thereto.

In certain embodiments, this disclosure relates to methods of treating or preventing heart malformation or cardiovascular disease comprising administering an effective amount of an individual agent or combination of agents such as thyroid hormone, a beta-adrenergic blocking agent, and/or DUSP5 or DUSP6 inhibitor.

In certain embodiments, this disclosure relates to methods of treating or preventing heart malformation or cardiovascular disease comprising administering an effective amount of thyroid hormone in combination with i) an agent that decreases DUSP5 and/or DUSP6 expression and/or ii) a beta-adrenergic blocking agent to a subject in need thereof.

In certain embodiments, this disclosure relates to methods disclosed herein which are a combination of beta-blocker and/or siRNA (to suppress DUSP5) and mitogens.

In certain embodiments, this disclosure relates to methods disclosed herein which are an agent for beta-adrenergic blockage in combination with thyroid hormone or mitogens for cardiac regeneration.

In certain embodiments, this disclosure relates to methods of treating or preventing heart malformation or cardiovascular disease comprising administering an effective amount a beta-adrenergic blocking agent to a subject in need thereof.

In certain embodiments, the method comprises administering an effective amount of thyroid hormone in combination with a beta-adrenergic blocking agent.

In certain embodiments, the beta-adrenergic blocking agent is selected from acebutolol, atenolol, betaxolol, bisoprolol, carteolol, carvedilol, esmolol, labetalol, metoprolol, nadolol, nebivolol, penbutolol, pindolol, propranolol, sotalol, timolol, or salts thereof.

In certain embodiments, the thyroid hormone and an agent that decrease DUSP5 expression and/or a beta-adrenergic blocking agent are administered in combination with a mitogen. In certain embodiments, the mitogen is neuregulin, IGF-1, YAP1, ERBB2.

In certain embodiments, the individual agent or combination of agents are administered in combination with a mitogen. In certain embodiments, the mitogen is neuregulin, IGF-1, YAP1, ERBB2.

In certain embodiments, the cardiovascular disease is selected from coronary artery disease, heart failure, cardiomyopathy, heart valve disease, and cardiac arrhythmias.

In certain embodiments, the subject is diagnosed with a heart attack, angina, or stroke, diabetes, angina pectoris due to coronary atherosclerosis, hypertension, migraine headaches, glaucoma, hyperthyroidism, fibromyalgia, generalized anxiety disorder, parkinsonian tremor, and atrial fibrillation.

In certain embodiments, this disclosure relates to methods of inducing proliferation of cardiomyocytes comprising administering an effective amount of an individual agent or combination of agents such as thyroid hormone, beta-adrenergic blocking agent, and/or DUSP5 or DUSP6 inhibitor.

In certain embodiments, this disclosure relates to methods of inducing proliferation of cardiomyocytes comprising administering an effective amount of thyroid hormone in combination with i) an agent that decreases DUSP5 and/or DUSP6 expression and/or ii) a beta-adrenergic blocking agent to a subject in need thereof.

In certain embodiments, the individual agent or combination of agents are administered in combination with a mitogen. In certain embodiments, the mitogen is neuregulin, IGF-1, YAP1, ERBB2.

In certain embodiments, this disclosure relates to methods of inducing proliferation of cardiomyocytes comprising administering an effective amount of thyroid hormone in combination with a beta-adrenergic blocking agent to a subject in need thereof.

In certain embodiments, this disclosure relates to methods of inducing proliferation of cardiomyocytes comprising administering an effective amount of a beta-adrenergic blocking agent to a subject in need thereof.

In certain embodiments, the beta-adrenergic blocking agent, DUSP5, or DUSP6 inhibitor is a small molecule.

In certain embodiments, the DUSP5 or DUSP6 inhibitor is a polysulfonated aromatic compound with a carbazole or naphthalene scaffold.

In certain embodiments, the DUSP5 or DUSP6 inhibitor is a compound selected from 2-benzylidene-3-(cyclohexylamino)-2,3-dihydro-1H-inden-1-one (BCI), carbazole-1,3,6-trisulfonic acid, carbazole-1,3,6,8-tetrasulfonic acid, 8-hydroxynaphthalene-1,6-disulfonic acid (RR527), 8-amino-4-hydroxynaphthalene-2-sulfonic acid (RR535), 8,8'-(diazene-1,2-diyl)bis(4-hydroxynaphthalene-2-sulfonic acid)(RR601), $1^2,3^2,5^2,7^2$-tetrahydroxy-1,3,5,7(1,3)-tetrabenzenacyclooctaphane-$1^5,3^5,5^5,7^5$-tetrasulfonic acid (RR701), derivatives, prodrugs, alkylesters, or alternative salts thereof.

In certain embodiments, the beta-adrenergic blocking agent, DUSP5 or DUSP6 inhibitor is siRNA or an antisense therapy.

In certain embodiments, the DUSP5 or DUSP6 inhibitor is siRNA comprising a sense region and an antisense region, wherein said sense region and said antisense region together form a duplex region, said antisense region and said sense region are each 18-30 nucleotides in length and said antisense region comprises a sequence a sequence selected from the group consisting of SEQ ID Nos: 1-120 or variant thereof.

In certain embodiments, the individual agent or combination of agents such as thyroid hormone, beta-adrenergic blocking agent, and/or DUSP5 or DUSP6 inhibitor is administered to a newborn within 1 to 7 days of birth.

In certain embodiments, the individual agent or combination of agents such as thyroid hormone, beta-adrenergic blocking agent, and/or DUSP5 or DUSP6 inhibitor is administered to a newborn within 8 to 14 days of birth.

In certain embodiments, the individual agent or combination of agents such as thyroid hormone, beta-adrenergic blocking agent, and/or DUSP5 or DUSP6 inhibitor is administered to a newborn within 15 to 21 days of birth.

In certain embodiments, the individual agent or combination of agents such as thyroid hormone, beta-adrenergic blocking agent, and/or DUSP5 or DUSP6 inhibitor is administered to a subject more than 21 days after birth.

In certain embodiments, the individual agent or combination of agents such as thyroid hormone, beta-adrenergic blocking agent, and/or DUSP5 or DUSP6 inhibitor is administered by intravenous (IV) injection, direct injection into the cardiac tissue, direct injection into apical cardiac tissue, or pericardial cavity.

In certain embodiments, the individual agent or combination of agents such as thyroid hormone, beta-adrenergic blocking agent, and/or DUSP5 or DUSP6 inhibitor is administered to a subject at risk of, exhibiting symptoms of, or diagnosed with a cardiovascular disease, condition, or injury.

In certain embodiments, the individual agent or combination of agents such as thyroid hormone, beta-adrenergic blocking agent, and/or DUSP5 or DUSP6 inhibitor is administered to a subject at risk of, exhibiting symptoms of, or diagnosed with heart disease, heart attack, stroke, heart failure, arrhythmia, heart valve disease, congenital heart defect, patent ductus arteriosus, ventricular septal defect, truncus arteriosus, atrioventricular septal defect, tetralogy of Fallot, transposition of the great arteries, hypoplastic left heart syndrome, tricuspid atresia, or heart murmur, for use in the treatment or prevention thereof.

In certain embodiments, this disclosure relates to in vitro methods of inducing proliferation of cardiomyocytes comprising administering an effective amount of an individual agent or combination of agents such as thyroid hormone, beta-adrenergic blocking agent, and/or DUSP5 or DUSP6 inhibitor to a cardiac cell. In certain embodiments, this disclosure relates to in vitro methods of inducing proliferation of cardiomyocytes comprising administering to a cardiac cell an effective amount of a thyroid hormone in combination with i) an agent that decreases DUSP5 and/or DUSP6 expression and/or ii) a beta-adrenergic blocking agent.

In certain embodiments, this disclosure relates to pharmaceutical composition comprising combinations of agents disclosed herein and a pharmaceutically acceptable excipient. In certain embodiments, the composition is in the form of a tablet, pill, capsule, granule or gel. In certain embodiments the pharmaceutical composition is in the form of a pH buffered saline solution.

Antisense and RNA Induced Silencing (RNAi) Therapies

Antisense therapy is a form of treatment for genetic disorders or infections. When the genetic sequence of a particular gene is known to be causative of a particular disease, it is possible to synthesize a strand of nucleic acid (DNA, RNA or a chemical analogue) that will bind to the messenger RNA (mRNA) produced by that gene and inactivate it, effectively turning that gene "off". This is because mRNA has to be single stranded for it to be translated. Alternatively, the strand might be targeted to bind a splicing site on pre-mRNA and modify the exon content of an mRNA.

This synthesized nucleic acid is termed an "anti-sense" oligonucleotide (AON) because its base sequence is complementary to the messenger RNA (mRNA), which is called the "sense" sequence Because nucleases that cleave the phosphodiester linkage in DNA are expressed in almost every cell, unmodified DNA molecules are generally degraded before they reach their targets. Therefore, antisense therapeutics are generally modified. Modifications include morpholino oligomers, peptide nucleic acids, and locked nucleic acids. A morpholino oligomer or a phosphorodiamidate morpholino oligomer (PMO) has DNA bases attached to a backbone of methylenemorpholine rings linked through phosphorodiamidate groups. Peptide nucleic acids (PNAs) are composed of repeating N-(2-aminoethyl)-glycine units linked by peptide bonds. The various purine and pyrimidine bases are linked to the backbone by a methylene bridge (—CH2-) and a carbonyl group (—(C═O)—). Locked nucleic acids (LNA) have a ribose moiety modified with an extra bridge connecting the 2' oxygen and 4' carbon. The bridge "locks" the ribose in the 3'-endo conformation, Double stranded RNA ("dsRNA") can used to inhibit protein expression. Double stranded RNA induced gene silencing can occur on at least three different levels: (i) transcription inactivation, which refers to RNA guided DNA or histone methylation; (ii) siRNA induced mRNA degradation; and (iii) mRNA induced transcriptional attenuation. mRNA degradation generally considered that the major mechanism of RNA induced silencing (RNA interference, or RNAi) in mammalian cells. Initial attempts to use RNAi in mammalian cells focused on the use of long strands of dsRNA. However, these attempts to induce RNAi met with limited success, due in part to the induction of the interferon response, which results in a general, as opposed to a target-specific, inhibition of protein synthesis. Thus, long dsRNA is not a viable option for RNAi in mammalian systems.

When short (18-30 bp) RNA duplexes are introduced into mammalian cells in culture, sequence-specific inhibition of target mRNA can be realized without inducing an interferon response. Certain of these short dsRNAs, referred to as small inhibitory RNAs ("siRNAs"), can act catalytically at sub-molar concentrations to cleave greater than 95% of the target mRNA in the cell. A description of the mechanisms for siRNA activity, as well as some of its applications are described in Provost et al. (2002) Ribonuclease Activity and RNA Binding of Recombinant Human Dicer, EMBO J 21(21): 5864-5874; Tabara et al. (2002) The dsRNA Binding Protein RDE-4 Interacts with RDE-1, DCR-1 and a DexH-box Helicase to Direct RNAi in *C. elegans*, Cell 109(7): 861-71; Ketting et al. (2002) Dicer Functions in RNA Interference and in Synthesis of Small RNA Involved in Developmental Timing in *C. elegans*; Martinez et al., Single-Stranded Antisense siRNAs Guide Target RNA Cleavage in RNAi, Cell 110(5):563; Hutvagner & Zamore (2002) A microRNA in a multiple-turnover RNAi enzyme complex, Science 297:2056.

From a mechanistic perspective, introduction of long double stranded RNA into plants and invertebrate cells is broken down into siRNA by a Type II endonuclease known as Dicer. Sharp, RNA interference-2001, Genes Dev. 2001, 15:485. Dicer, a ribonuclease-III-like enzyme, processes the dsRNA into 19-23 base pair short interfering RNAs with characteristic two base 3' overhangs. Bernstein, Caudy, Hammond, & Hannon (2001) Role for a bidentate ribonuclease in the initiation step of RNA interference, Nature 409:363. The siRNAs are then incorporated into an RNA-induced silencing complex (RISC) where one or more helicases unwind the siRNA duplex, enabling the complementary antisense strand to guide target recognition. Nykanen, Haley, & Zamore (2001) ATP requirements and small interfering RNA structure in the RNA interference pathway, Cell 107:309. Upon binding to the appropriate target mRNA, one or more endonucleases within the RISC cleaves the target to induce silencing. Elbashir, Lendeckel, & Tuschl (2001) RNA interference is mediated by 21- and 22-nucleotide RNAs, Genes Dev. 15:188.

The interference effect can be long lasting and may be detectable after many cell divisions. Moreover, RNAi exhibits sequence specificity. Kisielow, M. et al. (2002) Isoform-specific knockdown and expression of adaptor protein ShcA using small interfering RNA, J. Biochem. 363:1-5. Thus, the RNAi machinery can specifically knock down one type of transcript, while not affecting closely related mRNA. These properties make siRNA a potentially valuable tool for inhibiting gene expression and studying gene function and drug target validation. Moreover, siRNAs are potentially useful as therapeutic agents against: (1) diseases that are caused by over-expression or misexpression of genes; and (2) diseases brought about by expression of genes that contain mutations.

Successful siRNA-dependent gene silencing depends on a number of factors. One of the most contentious issues in RNAi is the question of the necessity of siRNA design, i.e., considering the sequence of the siRNA used. Early work in *C. elegans* and plants circumvented the issue of design by introducing long dsRNA (see, for instance, Fire, A. et al. (1998) Nature 391:806-811). In this primitive organism, long dsRNA molecules are cleaved into siRNA by Dicer, thus generating a diverse population of duplexes that can potentially cover the entire transcript. One or more have the potential to be highly functional, thereby silencing the gene of interest and alleviating the need for siRNA design.

The term "siRNA" refers to small inhibitory RNA duplexes that induce the RNA interference (RNAi) pathway. These molecules can vary in length (generally 18-30 base pairs) and contain varying degrees of complementarity to their target mRNA in the antisense strand. Some, but not all, siRNA have unpaired overhanging bases on the 5' or 3' end of the sense strand and/or the antisense strand. The term "siRNA" includes duplexes of two separate strands, as well as single strands that can form hairpin structures comprising a duplex region.

As used herein, unless otherwise specified, "non-functional siRNA" are defined as those siRNA that induce less than 50% (<50%) target silencing, "semi-functional siRNA" induce 50-79% target silencing, "functional siRNA" are molecules that induce 80-95% gene silencing, and "highly-functional siRNA" are molecules that induce great than 95% gene silencing. These definitions are not intended to be rigid and can vary depending upon the design and needs of the application. For instance, it is possible that a researcher attempting to map a gene to a chromosome using a functional assay, may identify an siRNA that reduces gene activity by only 30%. While this level of gene silencing may be "non-functional" for, e.g., therapeutic needs, it is sufficient for gene mapping purposes and is, under these uses and conditions, "functional." For these reasons, functional siRNA can be defined as those molecules having greater than 10%, 20%, 30%, 40%, 50%, 60%, 70%, 80%, or 90% silencing capabilities at 100 nM transfection conditions. Similarly, depending upon the needs of the study and/or application, non-functional and semi-functional siRNA can be defined as having different parameters. For instance, semi-functional siRNA can be defined as being those molecules that induce 20%, 30%, 40%, 50%, 60%, or 70% silencing at 100 nM transfection conditions. Similarly, non-functional siRNA can be defined as being those molecules that silence gene expression by less than 70%, 60%, 50%, 40%, 30%, or less.

```
siRNAs that Target Phosphatase 5 (DUSP5)
                                     (SEQ ID NO: 1)
AAACCCAUUUCACAAGAGA;

                                     (SEQ ID NO: 2)
AAACUGGGAUGGAGGAAUC;

                                     (SEQ ID NO: 3)
AAGAGAAGAUUGAGAGUGA;

                                     (SEQ ID NO: 4)
AAGCACAAUUUCCACCUUA;

                                     (SEQ ID NO: 5)
AAGGAAGGCCAAGCCAUUA;

                                     (SEQ ID NO: 6)
AAGGGUACUUGCUAGGUAU;

                                     (SEQ ID NO: 7)
ACCCUGAAAUGUUGUGUAG;

                                     (SEQ ID NO: 8)
ACUGUGGACUUCUGGGAUU;

                                     (SEQ ID NO: 9)
AGACUUUCUACUCGGAAUA;

                                    (SEQ ID NO: 10)
AGAGUUCGCCUUUUCAUUU;

                                    (SEQ ID NO: 11)
AGCAGGCUCUUCACUGAUA;
```

-continued (SEQ ID NO: 12)
AGUCAUACUUGAACUUGUC;

(SEQ ID NO: 13)
AGUGUUGCGUGGAUGUAAA;

(SEQ ID NO: 14)
CAAAUGGAUCCCUGUGGAA;

(SEQ ID NO: 15)
CAACGGCCACAUCCUGCUA;

(SEQ ID NO: 16)
CAACGUGGGAGAAAGAAGU;

(SEQ ID NO: 17)
CAAGAGCAACUGUGAUUUU;

(SEQ ID NO: 18)
CAAUAAAUACCUGCAGCAA;

(SEQ ID NO: 19)
CAAUACUGAAGACCUCAUU;

(SEQ ID NO: 20)
CACAAUUUCCACCUUAUUU;

(SEQ ID NO: 21)
CACCAGGCUUGCAAAUGAA;

(SEQ ID NO: 22)
CACCUACACUACAAAUGGA;

(SEQ ID NO: 23)
CAGCAACGUGGGAGAAAGA;

(SEQ ID NO: 24)
CAGCAGAAGCCCUGUGGCA;

(SEQ ID NO: 25)
CAGGGUGGCCCAGUUGAAA;

(SEQ ID NO: 26)
CAUGGUCUCGCCCAACUUU;

(SEQ ID NO: 27)
CAUUAGCUCCCACUUUCAA;

(SEQ ID NO: 28)
CAUUCCACCUCUUCUCAGA;

(SEQ ID NO: 29)
CCAAGAGCAACUGUGAUUU;

(SEQ ID NO: 30)
CCAAGCAGUUCCGCCUGAA;

(SEQ ID NO: 31)
CCACACGGCUGACAUUAGC;

(SEQ ID NO: 32)
CCACCUACACUACAAAUGG;

(SEQ ID NO: 33)
CCACUUUCAAGAAGCAAUA;

(SEQ ID NO: 34)
CCAUUUCACAAGAGAAGAU;

(SEQ ID NO: 35)
CCCAAGAGCAACUGUGAUU;

(SEQ ID NO: 36)
CCUGAAAUGUUGUGUAGAC;

(SEQ ID NO: 37)
CGGAAUAUCCUGAGUGUUG;

(SEQ ID NO: 38)
CUAAGACCCGUGUGAAUGU;

-continued (SEQ ID NO: 39)
CUGCAUGGCUUACCUUAUG;

(SEQ ID NO: 40)
GAAGAAAAGCAGUAUGUUA;

(SEQ ID NO: 41)
GAAGACCUCAUUCUGUCAU;

(SEQ ID NO: 42)
GAAGAUUGAGAGUGAGAGA;

(SEQ ID NO: 43)
GAAGCACAAUUUCCACCUU;

(SEQ ID NO: 44)
GAAGGAAGGCCAAGCCAUU;

(SEQ ID NO: 45)
GAAGGGUACUUGCUAGGUA;

(SEQ ID NO: 46)
GACAUUAGCUCCCACUUUC;

(SEQ ID NO: 47)
GACUUUGGCAUGAUUCUUA;

(SEQ ID NO: 48)
GAGAAAAGGCAGUUAUGAA;

(SEQ ID NO: 49)
GAGAAGAUUGAGAGUGAGA;

(SEQ ID NO: 50)
GAGACUUUCUACUCGGAAU;

(SEQ ID NO: 51)
GAGGCAAGGUCCUGGUCCA;

(SEQ ID NO: 52)
GAGGUAGUUGGUUGAAGUA;

(SEQ ID NO: 53)
GAGUGUUGCGUGGAUGUAA;

(SEQ ID NO: 54)
GAUAGGCCAUUUGCAGACA;

(SEQ ID NO: 55)
GAUAUGAGACUUUCUACUC;

(SEQ ID NO: 56)
GAUGUUGGCUUUUCUGGAU;

(SEQ ID NO: 57)
GAUUCUUAGUCAUACUUGA;

(SEQ ID NO: 58)
GCAACGUGGUACUACUUUU;

(SEQ ID NO: 59)
GCAAGAUGCUCCGCAAGGA;

(SEQ ID NO: 60)
GCACAAUUUCCACCUUAUU;

(SEQ ID NO: 61)
GCAGAAGCCCUGUGGCAAC;

(SEQ ID NO: 62)
GCAGCAACGUGGGAGAAAG;

(SEQ ID NO: 63)
GCAGCAGGCUCUUCACUGA;

(SEQ ID NO: 64)
GCAGGCUCUUCACUGAUAG;

(SEQ ID NO: 65)
GCAGUUAUGAAGCCAAUUC;

-continued

GCAUGACCCACCUACACUA; (SEQ ID NO: 66)

GCCAUGGGUUCUUCACUGA; (SEQ ID NO: 67)

GCGGCUCGCUCAACGUCAA; (SEQ ID NO: 68)

GCGGGUCUACUUCCUCAAA; (SEQ ID NO: 69)

GCUACAGGCCAGCUUAUGA; (SEQ ID NO: 70)

GCUGAUCACCGUCUAGUUG; (SEQ ID NO: 71)

GGAAGUGCCUACCAUGCAU; (SEQ ID NO: 72)

GGAGAAAAGGCAGUUAUGA; (SEQ ID NO: 73)

GGAGCAUGGUCUCGCCCAA; (SEQ ID NO: 74)

GGAGGCAGCAGGCUCUUCA; (SEQ ID NO: 75)

GGCCUUCGAUUACAUCAAG; (SEQ ID NO: 76)

GGGGAAAAGGCAAUAAUUU; (SEQ ID NO: 77)

GGUAGGUUCUCGGGACUGA; (SEQ ID NO: 78)

GUAGAUUCCAGGAGGAGAA; (SEQ ID NO: 79)

GUAGCAAGAUGUUGGCUUU; (SEQ ID NO: 80)

GUAGGGACAUGAUCAGCAU; (SEQ ID NO: 81)

GUAGUUGGUUGAAGUAGCA; (SEQ ID NO: 82)

GUGCUUAUGUCUCUUGUGA; (SEQ ID NO: 83)

GUUCUUCACUGACCUUGGA; (SEQ ID NO: 84)

UAAAACCCAUUUCACAAGA; (SEQ ID NO: 85)

UAAGACCCGUGUGAAUGUG; (SEQ ID NO: 86)

UAAGACUCAUGGACAUUUC; (SEQ ID NO: 87)

UACUUGAACUUGUCUCAUU; (SEQ ID NO: 88)

UAGACUUCAUUGACUGUGU; (SEQ ID NO: 89)

UAGCUCCCACUUUCAAGAA; (SEQ ID NO: 90)

UCAAGCAUAAGCCAAUAAA; (SEQ ID NO: 91)

UCACAAGAGAAGAUUGAGA; (SEQ ID NO: 92)

-continued

UCACCAGGCUUGCAAAUGA; (SEQ ID NO: 93)

UCACUGACCUUGGACUUUG; (SEQ ID NO: 94)

UCAUACCUGUGCAAUACUG; (SEQ ID NO: 95)

UCUAAGACCCGUGUGAAUG; (SEQ ID NO: 96)

UCUCAGAGCUCAGCAGAAG; (SEQ ID NO: 97)

UGACAUUAGCUCCCACUUU; (SEQ ID NO: 98)

UGACCAGGGUGGCCCAGUU; (SEQ ID NO: 99)

UGACCCACCUACACUACAA; (SEQ ID NO: 100)

UGAGGUAGUUGGUUGAAGU; (SEQ ID NO: 101)

UGGCUUACCUUAUGAAGAC; (SEQ ID NO: 102)

UGGGCCAGCUCCUGCAGUA; (SEQ ID NO: 103)

UUAAGACUCAUGGACAUUU; (SEQ ID NO: 104)

UUAUGAAGACCAAGCAGUU; (SEQ ID NO: 105)

UUCAAUGUCUGUCUCUGUU; (SEQ ID NO: 106)

UUUCAAGCAUAAGCCAAUA; (SEQ ID NO: 107)

UUUCAUACCUGUGCAAUAC; (SEQ ID NO: 108)

UUUGAACCCUGAAAUGUUG; and, (SEQ ID NO: 109)

UUUGAAGGAAGCACAAUUU. (SEQ ID NO: 110)

SC-60554: DUSP5 siRNA (human) is a pool of 3 different siRNA duplexes

A:

Sense: GCAUGGCUUACCUUAUGAATT (SEQ ID NO: 111)

Antisense: UUCAUAAGGUAAGCCAUGCTT (SEQ ID NO: 112)

B:

Sense: CGUCUAGUUGGGAAAGUAATT (SEQ ID NO: 113)

Antisense: UUACUUUCCCAACUAGACGTT (SEQ ID NO: 114)

C:

Sense: GUAGCAAGAUGUUGGCUUUTT (SEQ ID NO: 115)

Antisense: AAAGCCAACAUCUUGCUACTT (SEQ ID NO: 116)

sc-60555: DUSP5 siRNA (mouse) is a pool of 2 different siRNA duplexes:

A:

Sense: GCAUGGCUUACCUCAUGAATT (SEQ ID NO: 117)

Antisense: UUCAUGAGGUAAGCCAUGCTT (SEQ ID NO: 118)

B:

Sense: GACAGCUCCUUCAGUAUGATT (SEQ ID NO: 119)

Antisense: UCAUACUGAAGGAGCUGUCTT (SEQ ID NO: 120)

Any of the methods disclosed herein can be used to silence one or more genes by introducing an siRNA selected, or designed, in accordance with any of the methods disclosed herein. The siRNA(s) can be introduced into the cell by any method known in the art, including passive uptake or through the use of one or more vectors.

Preferably, the siRNA is applied to a cell through transfection, employing standard transfection protocols. These methods are well known to persons skilled in the art and include the use of lipid-based carriers, electroporation, cationic carriers, and microinjection. Further, one could synthesize equivalent DNA sequences (either as two separate, complementary strands, or as hairpin molecules) instead of siRNA sequences and introducing them into cells through vectors. Once in the cells, the cloned DNA could be transcribed, thereby forcing the cells to generate the siRNA. Examples of vectors suitable for use with the present application include but are not limited to the standard transient expression vectors, adenoviruses, retroviruses, lentivirus-based vectors, as well as other traditional expression vectors. Any vector that has an adequate siRNA expression and procession module may be used. Furthermore, certain chemical modifications to siRNAs, including but not limited to conjugations to other molecules, may be used to facilitate delivery. For certain applications, it may be preferable to deliver molecules without transfection by simply formulating in a physiological acceptable solution.

Formulations

Pharmaceutical compositions disclosed herein may be combinations of agents for uses disclosed herein in the form of a single pharmaceutically acceptable composition. In certain embodiments, the pharmaceutical composition is in the form of a tablet, capsule, pill, or solution for injection. In certain embodiments, the pharmaceutical composition is in sterilized and pH buffered aqueous solution, e.g., phosphate buffered solution, optionally comprising a saccharide or polysaccharide.

When the compounds of the disclosure contain an acidic group as well as a basic group, the compounds of the disclosure may also form internal salts, and such compounds are within the scope of the disclosure. When a compound contains a hydrogen-donating heteroatom (e.g. NH), salts are contemplated to covers isomers formed by transfer of said hydrogen atom to a basic group or atom within the molecule.

Pharmaceutically acceptable salts of the compounds include the acid addition and base salts thereof. Suitable acid addition salts are formed from acids that form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminum, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein may be administered in the form of prodrugs. A prodrug can include a covalently bonded carrier that releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in the compounds. Methods of structuring a compound as prodrugs can be found in the book of Testa and Mayer, Hydrolysis in Drug and Prodrug Metabolism, Wiley (2006). Typical prodrugs form the active metabolite by transformation of the prodrug by hydrolytic enzymes, the hydrolysis of amide, lactams, peptides, carboxylic acid esters, epoxides or the cleavage of esters of inorganic acids.

Pharmaceutical compositions for use in the present disclosure typically comprise an effective amount of a compound and a suitable pharmaceutical acceptable carrier. The preparations may be prepared in a manner known per se, which usually involves mixing the at least one compound according to the disclosure with the one or more pharmaceutically acceptable carriers, and, if desired, in combination with other pharmaceutical active compounds, when necessary under aseptic conditions. Reference is again made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

Generally, for pharmaceutical use, the compounds may be formulated as a pharmaceutical preparation comprising at least one compound and at least one pharmaceutically acceptable carrier, diluent or excipient and/or adjuvant, and optionally one or more further pharmaceutically active compounds.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the disclosure, e.g. about 10, 25, 50, 100, 200, 300 or 400 mg per unit dosage.

The compounds can be administered by a variety of routes including the oral, ocular, rectal, transdermal, subcutaneous, intravenous, intramuscular or intranasal routes, depending mainly on the specific preparation used. The compound will generally be administered in an "effective amount", by which is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

Depending upon the manner of introduction, the compounds described herein may be formulated in a variety of ways. Formulations containing one or more inhibitors can be prepared in various pharmaceutical forms, such as granules, tablets, capsules, suppositories, powders, controlled release formulations, suspensions, emulsions, creams, gels, ointments, salves, lotions, or aerosols and the like. Preferably, these formulations are employed in solid dosage forms suitable for simple, and preferably oral, administration of precise dosages. Solid dosage forms for oral administration include, but are not limited to, tablets, soft or hard gelatin or non-gelatin capsules, and caplets. However, liquid dosage forms, such as solutions, syrups, suspension, shakes, etc. can also be utilized. In another embodiment, the formulation is administered topically. Suitable topical formulations include, but are not limited to, lotions, ointments, creams, and gels. In a preferred embodiment, the topical formulation is a gel. In another embodiment, the formulation is administered intranasally.

Formulations containing one or more of the compounds described herein may be prepared using a pharmaceutically acceptable carrier composed of materials that are considered safe and effective and may be administered to an individual without causing undesirable biological side effects or unwanted interactions. The carrier is all components present in the pharmaceutical formulation other than the active ingredient or ingredients. As generally used herein "carrier" includes, but is not limited to, diluents, binders, lubricants, disintegrators, fillers, pH modifying agents, preservatives, antioxidants, solubility enhancers, and coating compositions.

Carrier also includes all components of the coating composition which may include plasticizers, pigments, colorants, stabilizing agents, surfactants, and glidants. Delayed release, extended release, and/or pulsatile release dosage formulations may be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, PA: Williams and Wilkins, 1995). These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins, zein, shellac, and polysaccharides.

Optional pharmaceutically acceptable excipients present in the drug-containing tablets, beads, granules or particles include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropyl methylcellulose, hydroxypropyl cellulose, ethylcellulose, and magnesium aluminum silicate, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, arginine, gums or cross-linked polymers, such as cross-linked PVP.

Stabilizers are used to inhibit or retard drug decomposition reactions which include, by way of example, oxidative reactions.

Surfactants may be anionic, cationic, amphoteric or nonionic surface-active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, stearoyl monoisopropanolamide, and polyoxyethylene hydrogenated tallow amide. Examples of amphoteric surfactants include sodium N-dodecyl-beta-alanine, sodium N-lauryl-beta-iminodipropionate, myristoamphoacetate, lauryl betaine, and lauryl sulfobetaine.

If desired, the tablets, beads, granules, or particles may also contain minor amount of nontoxic auxiliary substances such as wetting or emulsifying agents, dyes, pH buffering agents, or preservatives.

The concentration of the inhibitor(s) to carrier and/or other substances may vary from about 0.5 to about 100 wt % (weight percent). For oral use, the pharmaceutical formulation will generally contain from about 5 to about 100% by weight of the active material. For other uses, the pharmaceutical formulation will generally have from about 0.5 to about 50 wt % of the active material.

EXAMPLES

DUSP5 Triggers and Maintains Cell Cycle Block in Postnatal Murine Cardiomyocytes Experimental evidence indicates cardiomyocyte endowment of the murine heart increases during preadolescence—that is, during the second week of life. This increase is triggered by a rise in circulating thyroid hormone ($T_3$) that starts at around postnatal day-11. These findings questioned long-held views about timing of cardiomyocyte cell cycle withdrawal in murine hearts. It is generally believed that murine cardiomyocytes withdraw from the cell cycle after postnatal day 6. Studies suggested that this developmental process does not occur until after the second week of life. $T_3$ has long been regarded as a cardiomyocyte maturation factor causing cardiomyocytes to hypertrophy. The fact that experimental evidence indicates developmental increases in $T_3$ cause cardiomyocytes to proliferate contradicts long-held views about the way by which this hormone regulates early postnatal heart growth: by cardiomyocyte hypertrophy, hyperplasia, or both.

The mechanism by which murine cardiomyocytes withdraw from the cell cycle and its timing were examined. Cell cycle block in post-neonatal cardiomyocytes occurs during the second week of life, progressively from left ventricular base to its apex, that is concordant with sympathetic innervation of the heart. This results in β1-adrenergic receptor-mediated expression of dual specificity phosphatase 5 (DUSP5). DUSP5 is a nuclear phosphatase that inactivates phosphorylated-ERK1/2; because nuclear ERK1/2 signaling is the common mediator of proliferative signaling by growth factors, integrins and a host of other mitogens, its expression in postnatal cardiomyocytes makes them resistant to proliferation. Due to the unique pattern of DUSP5 expression during early postnatal heart development, left ventricular cardiomyocytes at the base of the heart withdraw from the cell cycle immediately after postnatal day-6, whereas those residing at the ventricular apex retain proliferative capacity until the end of the second week of life. Conclusions about the timing of cardiomyocyte cell cycle withdrawal must, therefore, take into consideration this critical region-specific difference in cardiomyocyte proliferative capacity if the timing of cardiomyocyte cell cycle withdrawal is to be fully understood—a factor not previously appreciated.

Importantly, experimental evidence indicates acute β1-adrenergic receptor blockade suppresses DUSP5 expression in cardiomyocytes, which restores cardiomyocyte proliferative capacity even in adult 6-month-old hearts. This therapy, when combined with $T_3$ administration, causes hyperplastic heart growth in adult mice with important consequences for left ventricular function; a finding of potential major clinical significance for building muscle in failing hearts.

To determine when and how proliferative capacity is lost in murine cardiomyocytes. (1) A $T_3$ challenge coupled with genetic lineage tracing was used to assess in vivo cardiomyocyte proliferative capacity in post-neonatal hearts. Post-neonatal cardiomyocytes residing in the left ventricular (LV) apex, but not base, proliferated in response to $T_3$; this mitogenic effect was lost by P16. (2) The mechanism involved nuclear ERK1/2 signaling consequent on $T_3$-mediated enhancement of IGF-1 and IGF-1R expression. (3) The loss of $T_3$-stimulated proliferation in LV basal cardiomyocytes was caused by developmental expression of dual specificity phosphatase 5 (DUSP5), a nuclear phosphatase that inactivates phosphorylated-ERK1/2. (4) In early postnatal heart development, spatial and temporal restriction of DUSP5 expression is regulated by β1-adrenergic receptor activation commensurate with progressive sympathetic innervation of the heart from base to apex. (6) Combination therapy with $T_3$ plus a β1-adrenergic receptor blocker stimulated in vivo cardiomyogenesis and enhanced LV contractile function in adult hearts.

These findings indicate cell cycle block in post-neonatal cardiomyocytes occurs progressively from LV base to its apex during the second week of life and is caused by β1-adrenergic receptor-mediated expression of DUSP5. A combination of β1-adrenergic receptor blockade plus $T_3$ or derivatives can be useful for restoring cardiomyogenesis in diseased hearts.

Compound Administration $T_3$ was administered, intraperitoneally, to each mouse at the dose indicated. Vehicle was administered by the same route and animals thus treated served as controls. Phosphate buffered saline (PBS) was the vehicle for $T_3$, and soybean oil (Sigma, S7381) was the vehicle for 4-hydroxytamoxifen. DUSP5 or β1-adrenergic receptor-specific siRNA or scrambled siRNA (control) was administered using in vivo-jetPEI®, (VWR, 89129-960). Litters were not used if one or more mouse in the litter was observed to be sick or stunted. P7 and older mice were first anesthetized with 5% isoflurane and then hearts were harvested for further processing. Hearts were also collected at 12, 24 and 40 h after $T_3$ or vehicle treatment and ventricular cardiomyocytes were prepared from the apex and base for immunoblotting, RT-qPCR or immunocytochemistry. Hearts were also collected at various ages after birth for immunoblotting, immunocytochemistry, immunohistochemistry and cardiomyocyte number estimation.

Echocardiograph Analysis of Mice after $T_3$/β1-Adrenergic Receptor Blocker Therapy Approximately 6-month-old mice were used. These mice were treated with the β1-adrenergic receptor blocker, metoprolol succinate (6 μg/g daily, i.p.) or vehicle (as control) for 19 days. On day-14 of this therapy, mice were additionally given 5 daily injections of $T_3$ (2 ng/g, i.p.) or vehicle. At 2 and 4 weeks after the cessation of $T_3$/β1-adrenergic receptor blocker mono- or combination therapy, the body weights of these mice were measured as well as their cardiac dimensions and function using transthoracic echocardiography.

LV Apical Cardiomyocytes of Early Post-Neonatal Hearts Retain Proliferative Capacity An acute in vivo $T_3$ challenge was used to identify post-neonatal LV cardiomyocytes that retain proliferative capacity. Increases in myocardial cell cycle-promoting cyclins was explored as a surrogate for identifying cardiomyocytes that are able to enter the cell cycle. After 40 h an in vivo $T_3$ challenge in P8 mice, expression of cyclins D1, A2 and B1—which promote G1/S phase transition, S phase, and G2/M phase transition, respectively—was increased only in the LV and, that within the LV, these cyclins showed 2.5-100-fold higher expression in the apex than in the base (P<0.001) (FIGS. 1A and B).

Figure 1C:
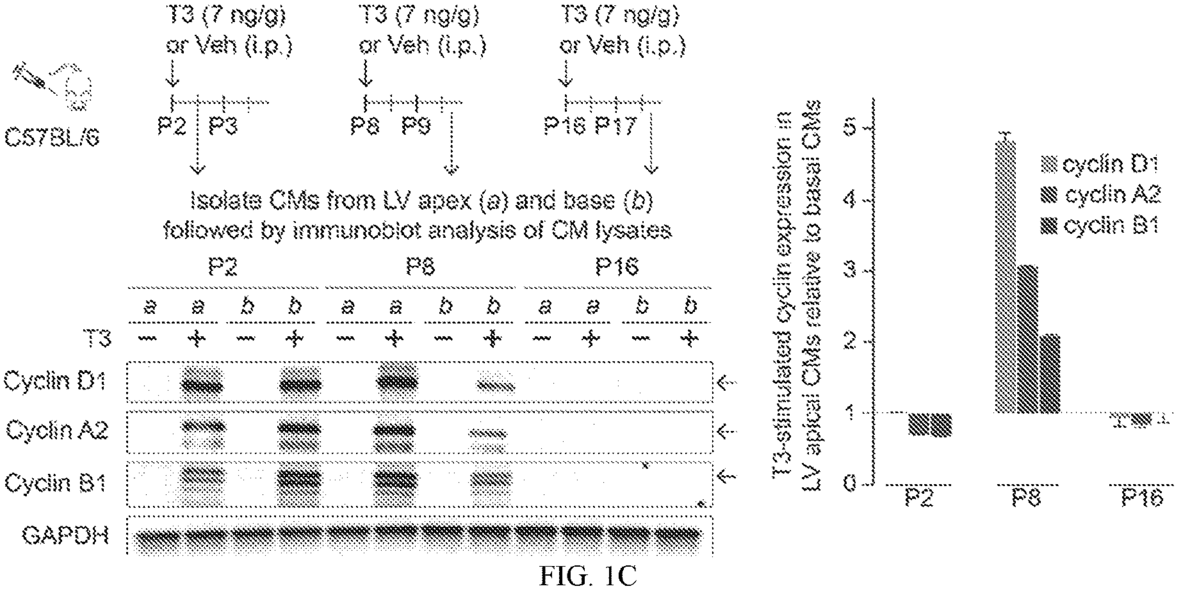
FIG. 1C shows representative immunoblots indicating expression levels of proteins in whole cell lysates of cardiomyocytes of the LV apex (a) and base (b) at P2 (neonatal), P8 (post-neonatal/early preadolescent) and P16 (preadolescent), both with and without in vivo $T_3$ treatment.

The ontogeny of the $T_3$-stimulated cyclin response during early heart development was examined by comparing cardiomyocytes from the LV apex and the base. In neonatal hearts, $T_3$ increased cyclins D1/A2/B1 similarly in LV apical and basal cardiomyocytes (FIG. 1C). In P8 hearts, $T_3$ increased these cyclins ~2-5-fold more in apical cardiomyocytes than in basal cardiomyocytes (FIG. 1C). However, $T_3$ did not increase cyclins in either apical or basal P16 cardiomyocytes. These findings indicate that, for ~1 week beyond the neonatal period, a population of LV cardiomyocytes is able to enter the cell cycle.

Figure 2A:
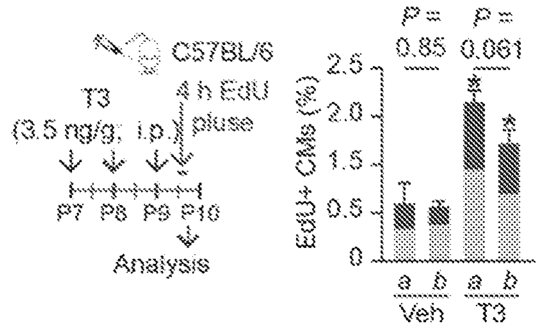
FIG. 2A shows data indicating cardiomyocytes (CM) of the early post-neonatal LV apex retain proliferative capacity. Cardiomyocytes were identified by cTnT labeling. $T_3$ effects on DNA synthesis (EdU) (A) and in LV apical (a) and basal (b) cardiomyocytes.
Figure 2B:
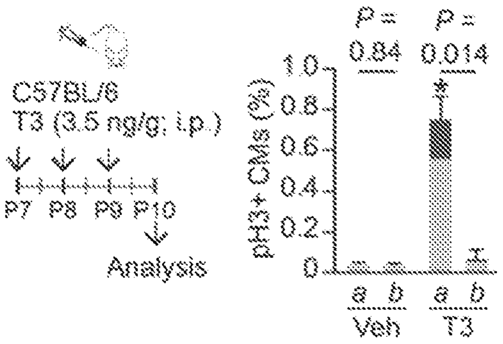
FIG. 2B shows data on mitosis (pH3).
Figure 2C:
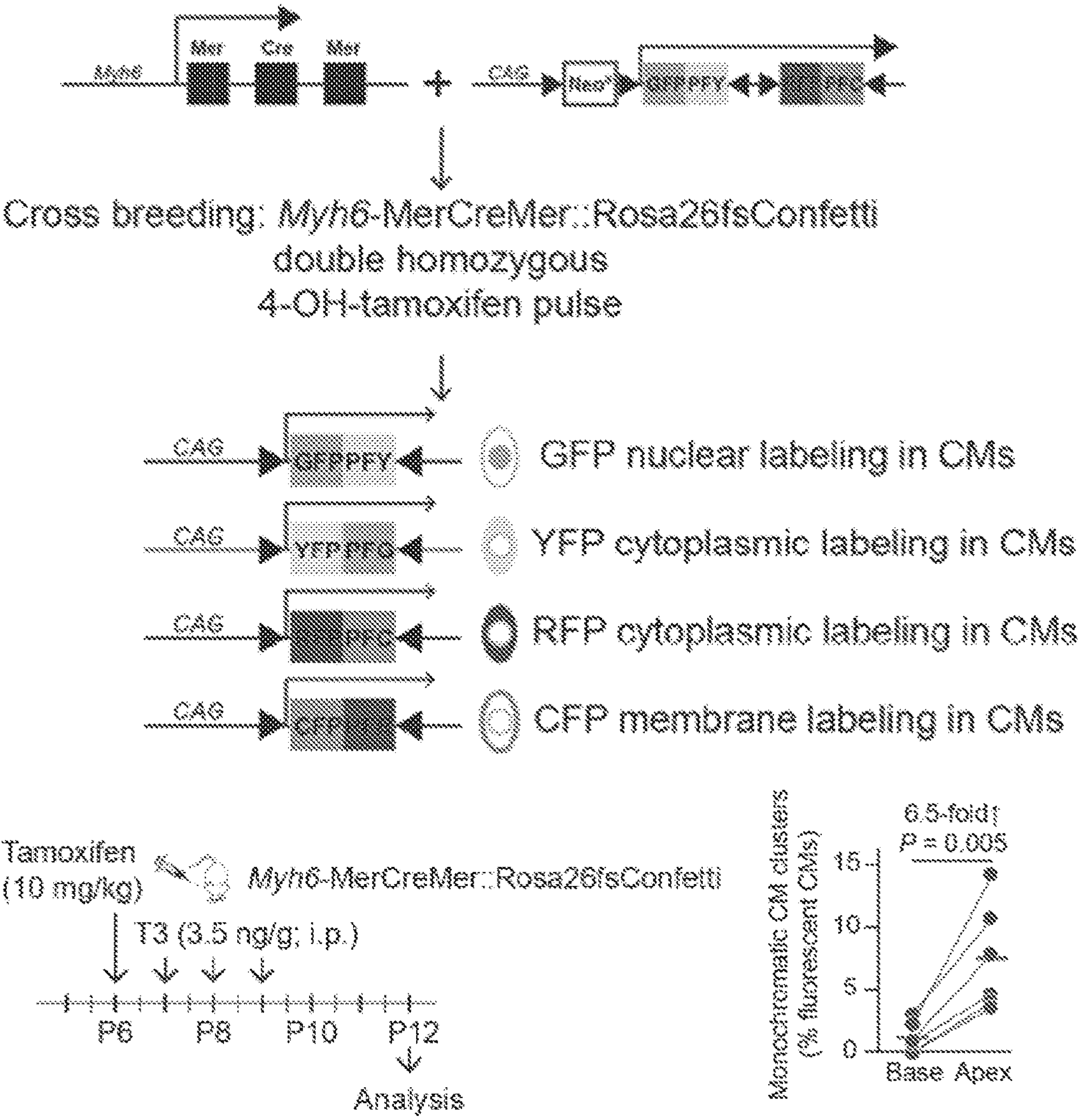
FIG. 2C illustrates multicolor labeling of post-neonatal mouse LV cardiomyocytes. Limited 4-hydroxytamoxifen-induced recombination of paired loxP sites (black triangles) leads to expression of green fluorescent protein (GFP), yellow fluorescent protein (YFP), red fluorescent protein (RFP) or cyan fluorescent protein (CFP) in a few cardiomyocytes, randomly positioned within the entire LV. Insets show examples of monochromatic clusters.

Experiments were performed to determine whether $T_3$-stimulated cell cycle entry in LV apical cardiomyocytes ends in mitosis and cell replication. Immunocytochemical studies on cardiomyocytes isolated from the post-P8 LV apex revealed that in vivo $T_3$ administration increased the number of cardiomyocytes in S phase (5-ethynyl-2'-deoxyuridine+ (EdU)+) and in mitosis (phosphorylated histone H3+(pH3)+) (FIGS. 2A and 2B). Although S phase and mitosis were observed in both mono- and binucleated LV apical cardiomyocytes, their occurrence as a percentage of cell type was greater in mononuclear cells (FIG. 2B). While an increase in S phase was observed in LV basal cardiomyocytes, these cells did not enter mitosis (FIGS. 2A and 2B).

Mitosis can result in cell replication, or it can stall prior to karyokinesis or cytokinesis. To determine if LV apical cardiomyocytes undergo cell replication, multicolor clonal analysis was used in double-transgenic Myh6-MerCreMer::Rosa26fs-Confetti mice to record the proliferative strategies of individual cardiomyocytes of the apex relative to those of the base. Limited Cre activation (by administration of 10 mg/kg 4-hydroxytamoxifen to P6 mice) yielded labeling in ~5% of ventricular cardiomyocytes with one of 4 unique colors. $T_3$ given daily over 3 days (P7-P9) increased the frequency of monochromatic cardiomyocyte clusters by ~6.5-fold in the LV apex relative to the base of the same mouse heart. The majority of monochromatic cardiomyocyte clusters in the LV apex consisted of 2 cells, and were distributed throughout the tissue section, indicating that cardiomyocyte proliferation resulted from multiple individual cell replication events rather than clonal expansion of a few highly proliferative cells.

Figure 2D:
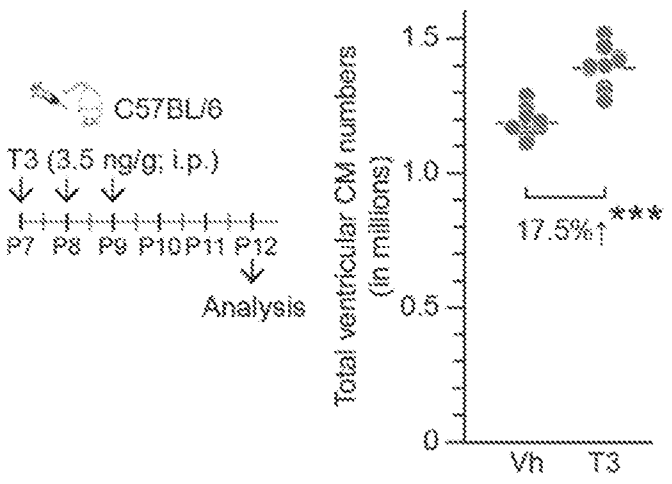
FIG. 2D show data on total ventricular cardiomyocyte cell numbers.

To determine the effect of $T_3$ on the ventricular cardiomyocyte population in early post-neonatal mice, $T_3$ daily (i. p.), was administered from P7 to P9. At P12, hearts were enzymatically disaggregated and cell suspensions created from the cardiac ventricles. Digestion efficiencies were ~98%. Cardiomyocytes in these cell suspensions, identified by their size and by rod shape, were counted using a hemocytometer. $T_3$ increased ventricular cardiomyocyte numbers by ~18% (FIG. 2D), which indicates an average replication rate of 3.6%/day between P7 and P12.

Figure 3A:
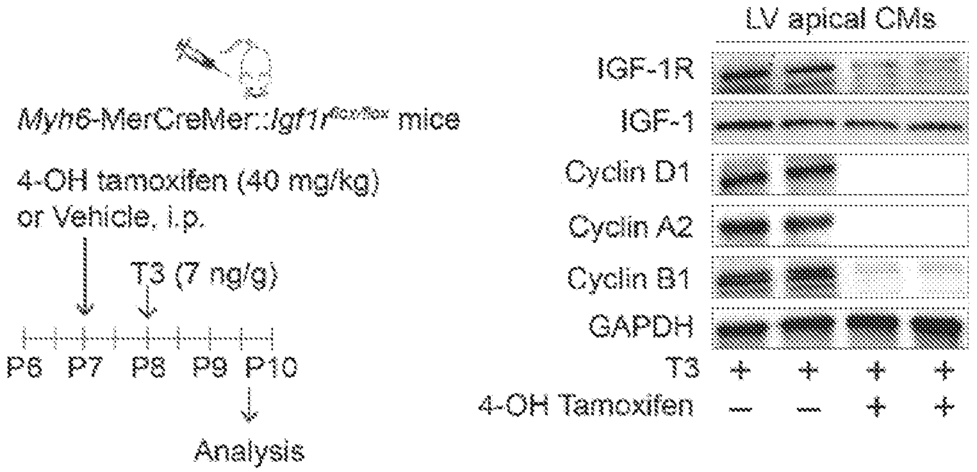
FIG. 3A shows data indicating $T_3$-stimulated cyclin expression in early post-neonatal apical cardiomyocytes is mediated by IGF-1/IGF-1R signaling. In vivo cardiomyocyte-specific IGF-1R knockdown prevented $T_3$-induced increases in cyclins in LV apical cardiomyocytes. Floxed Igf1r mice (Igf1rflox/flox) were crossed with Myh6-MerCreMer mice in which the transgene consists of the mouse cardiac-specific Myh6 promoter directing expression of a 4-hydroxytamoxifen-inducible Cre recombinase (MerCreMer) in postnatal cardiomyocytes. To achieve such a cell type-specific knockdown, 4-hydroxytamoxifen was administered at P6 to Myh6-MerCreMer::Igf1rflox/flox mice.
Figure 3B:
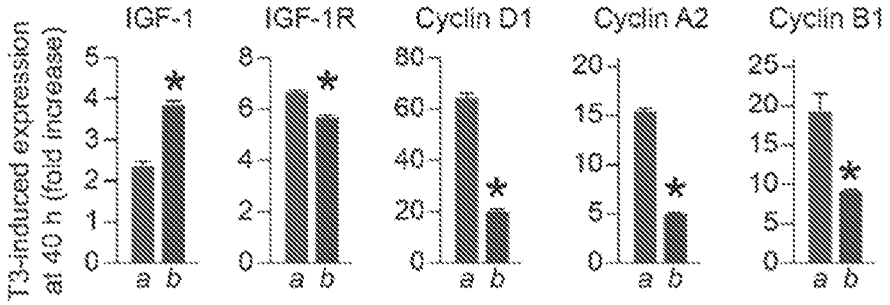
FIG. 3B shows data from immunoblots indicating expression levels of indicated proteins in post-neonatal apical (a) and basal (b) cardiomyocytes after in vivo $T_3$ or vehicle treatment. Bar graph shows fold changes in expression 40 h after $T_3$ treatment, relative to vehicle treatment.

DUSP5 Expression Causes Loss of Proliferative Competence in Post-Neonatal Cardiomyocytes Developmental increases in $T_3$ stimulate insulin-like growth factor-1 (IGF-1) receptor (IGF-1R) signaling in early post-neonatal cardiomyocytes. Experiments indicate that IGF-1R expression is required for $T_3$-stimulated cyclin expression in P8 LV apical cardiomyocytes (FIG. 3A). However, while $T_3$-stimulated expression of IGF-1/IGF-1R is comparable in basal and apical cardiomyocytes (FIG. 3B), expression of cyclins D1, A2 and B1 is ~2-3-fold lower in basal cardiomyocytes (P<0.001) (FIG. 3B). These data suggest that IGF-1R proliferative signaling is intrinsically inhibited in basal cardiomyocytes.

Figure 4A:
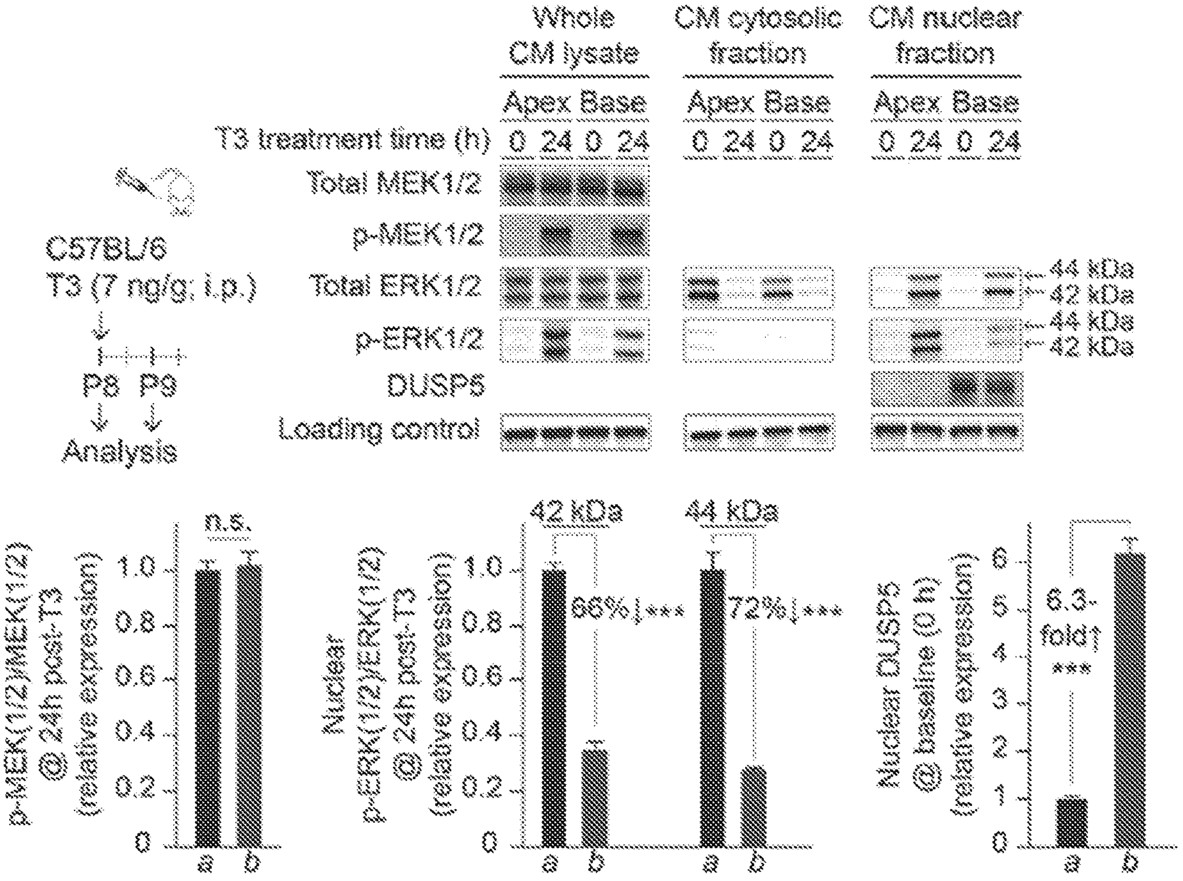
FIG. 4A shows data indication DUSP5 inhibits $T_3$-induced proliferative signaling in early post-neonatal LV cardiomyocytes (CMs). Protocol for $T_3$ administration, cardiomyocyte isolation and preparation of whole cell, cytosolic or nuclear lysates for immunoblotting is shown in the schematic. Representative immunoblots show expression levels of indicated proteins in cardiomyocytes of the LV apex and base at 0 (baseline) and 24 h after $T_3$ administration. Bar graphs show quantification of the phospho-MEK1/2, and nuclear phospho-ERK1/2 and DUSP5.

Proliferative signaling by growth factors involves Ras/Raf/mitogen-activated protein kinase (MAPK) kinase (MEK)/extracellular signal-regulated kinase (ERK) signaling. MEK1/2 activate ERK1/2 by phosphorylating T202 and Y204, which is required for ERK1/2 translocation to the nucleus. Sustained ERK1/2 phosphorylation in the nucleus activates multiple transcription factors ultimately resulting in effector protein synthesis and cell proliferation. A single dose of $T_3$ was administered to P8 mice, and cardiomyocytes were isolated from the LV apex or base either immediately after $T_3$ administration (0 h) or after 24 h. $T_3$ increased MEK1/2 phosphorylation (5218/5222) and nuclear translocation of ERK1/2 similarly in apical and basal cardiomyocytes (FIG. 4A). However, the fraction of nuclear ERK1/2 that remained phosphorylated at 24 h post-$T_3$ treatment was ~70% lower in LV basal cardiomyocytes (FIG. 4A).

Figure 4B:
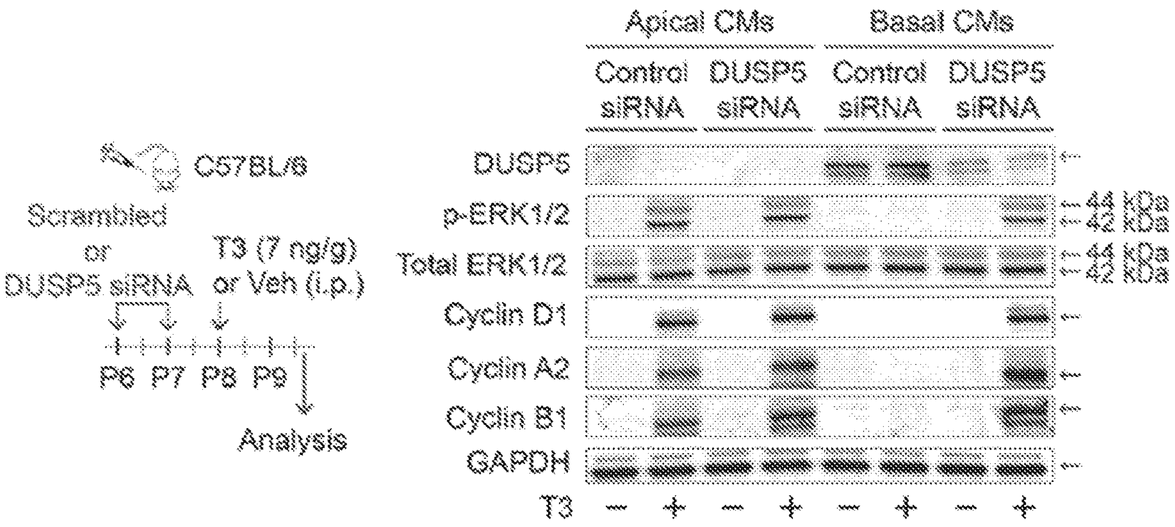
FIG. 4B shows data where DUSP5 or scrambled (control) siRNAs were administered intraperitoneally (i.p.) to mice at P6 and P7, followed by $T_3$ (+) or vehicle (−) treatment at P8. siRNAs were dissolved in the in vivo-jetPEI and 10% glucose mixture. Forty hours later, CMs were isolated and whole cell lysates prepared. Lysates were then subjected to immunoblotting for the indicated proteins.
Figure 4C:
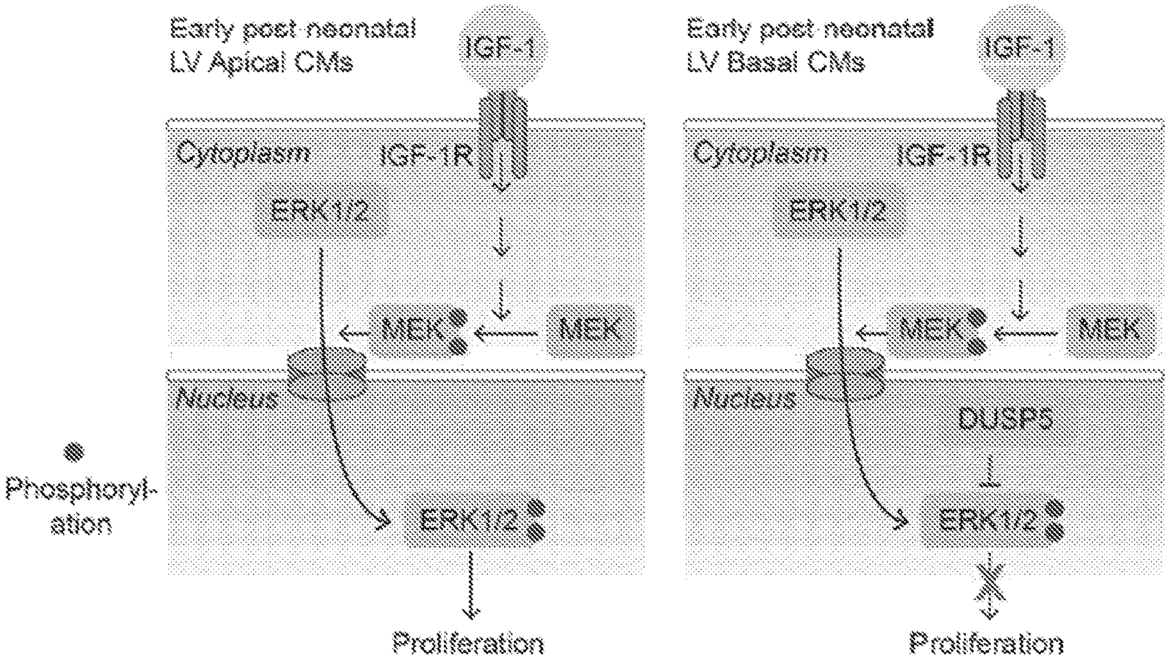
FIG. 4C shows a model illustrating the proposed mechanism underlying the selective loss of nuclear phosphorylated ERK1/2 in LV basal cardiomyocytes of early post-neonatal mice.

These data suggest that cytoplasmic ERK1/2 phosphorylation by $T_3$/IGF-1R is similar in apical and basal P8-P9 LV cardiomyocytes, but after nuclear translocation its dephosphorylation is more rapid in basal cardiomyocytes. The potential involvement of the dual-specificity (T/Y) MAPK phosphatase, DUSP5, was studied. DUSP5 is an inducible nuclear phosphatase that attenuates MAPK signaling by specifically binding and dephosphorylating p-ERK1/2. DUSP5's involvement was supported by the finding that levels of DUSP5 were ~6-fold higher in LV basal versus apical cardiomyocytes (FIG. 4A). In vivo siRNA knockdown of DUSP5 mRNA depleted DUSP5 in LV basal cardiomyocytes, and in this setting $T_3$ stimulated ERK1/2 phosphorylation and expression of cyclins (FIG. 4B). Thus, DUSP5 inhibits $T_3$-stimulated ERK1/2 phosphorylation in post-neonatal LV basal cardiomyocytes (FIG. 4C).

Figure 5A:
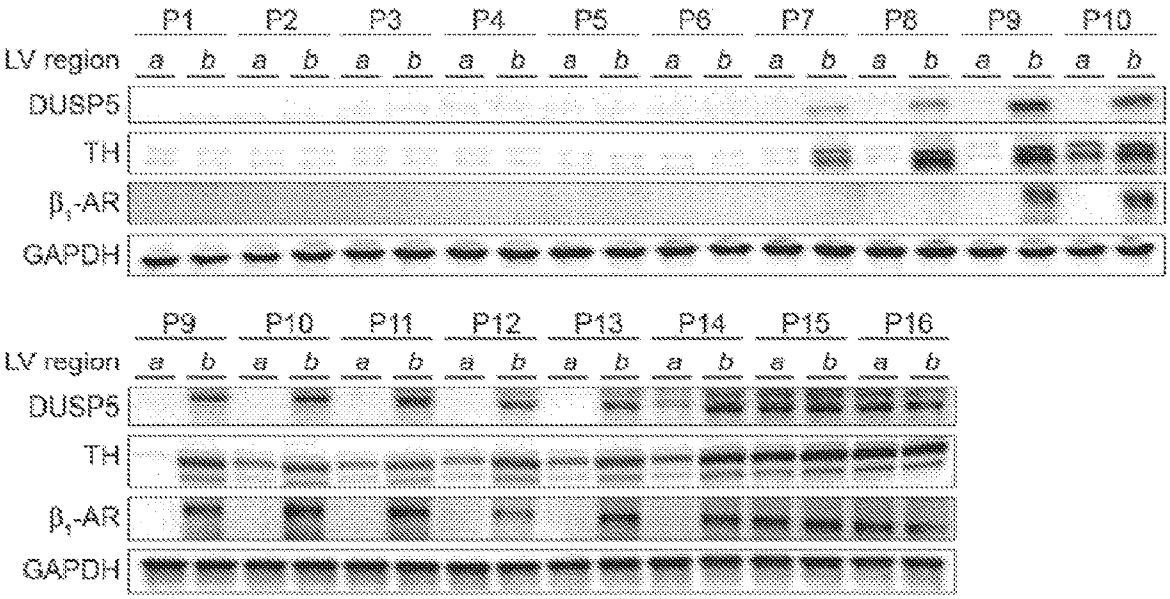
FIG. 5A shows data indicating acute DUSP5 depletion reverses cell cycle block in LV cardiomyocytes (CMs) of 6-week-old mice. Representative immunoblots showing developmental changes in myocardial DUSP5, tyrosine hydroxylase and β1-adrenergic receptor (β1-AR) levels in the LV apex (a) and base (b) of early postnatal hearts.

To determine if the developmental pattern of DUSP5 expression is consistent with a role in suppression of the proliferative potential of murine hearts, changes in DUSP5 expression were examined in the LV apical and basal myocardium from birth to P16. DUSP5 was not detectable in the LV apex or base of neonatal animals (FIG. 5A). After P6, DUSP5 expression increased in the LV base and remained high. In the LV apex, DUSP5 expression was first observed at P14, and by P15, it was uniformly high throughout the LV. This temporal expression of DUSP5 in the LV is concordant with developmental differences in $T_3$-stimulated cardiomyocyte cyclin expression (FIG. 1C).

Figure 5B:
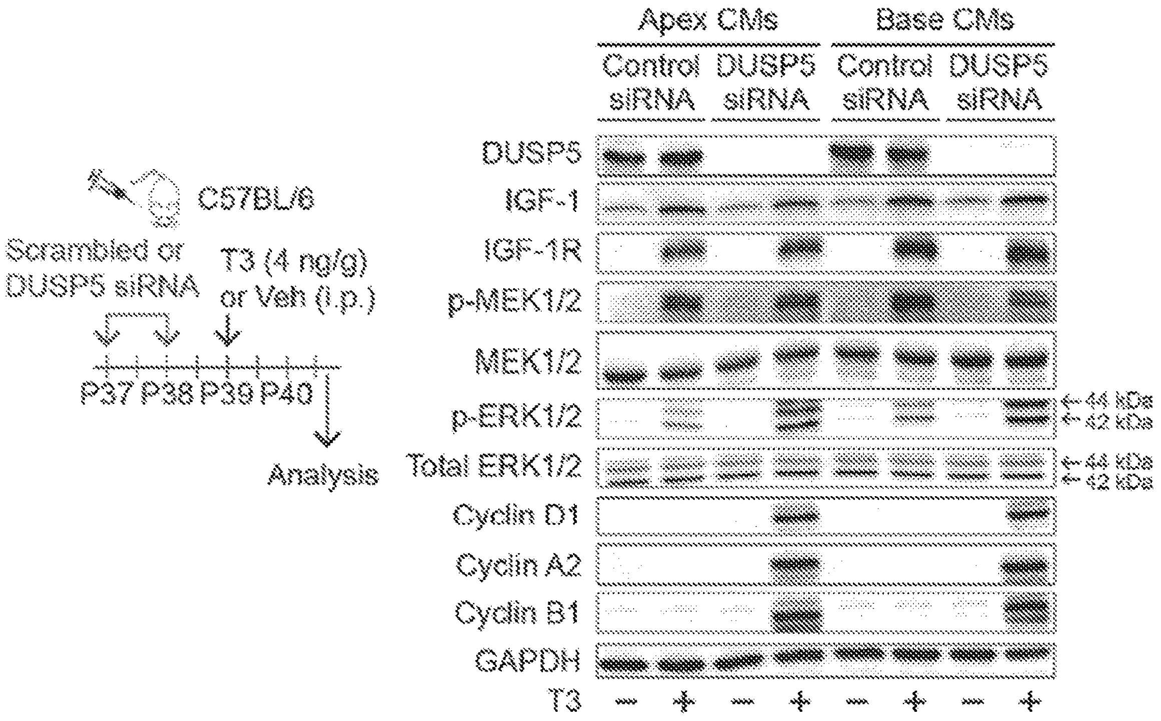
FIG. 5B shows DUSP5 knockdown in cardiomyocytes of the LV apex and base, using acute in vivo siRNA treatment, increased ERK1/2 phosphorylation and cyclin expression in response to $T_3$. Scrambled siRNA was used as a siRNA control. Whole cell lysates were used in these studies.
Figure 5C:
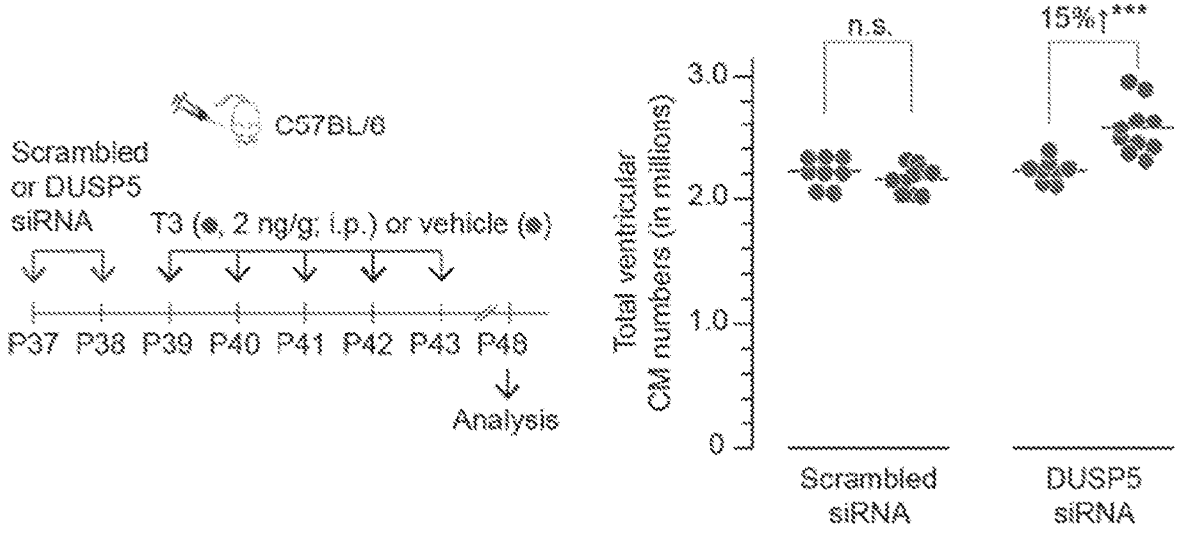
FIG. 5C shows data indicating total ventricular cardiomyocyte numbers were greater in $T_3$-(dots) versus vehicle (dots)-treated mice that had been pretreated with DUSP5 siRNA, but not in those pretreated with scrambled siRNA.

Additional experiments were performed to determine whether DUSP5 expression in adult cardiomyocytes necessary to sustain cell cycle block. In 6-week-old adult mice, acute DUSP5 depletion by siRNA enhanced $T_3$-induced ERK1/2 phosphorylation and cyclin expression in LV cardiomyocytes, without influencing IGF-1/IGF-1R expression or MEK1/2 phosphorylation (FIG. 5B). Importantly, acute DUSP5 depletion coupled with $T_3$ treatment increased the cardiomyocyte endowment of adult hearts (FIG. 5C). Collectively, the results of these experiments indicate that DUSP5 blocks the cell cycle in cardiomyocytes as its expression increases progressively from the LV base during the early post-neonatal period to the apex during preadolescence. It then maintains this block as cardiomyocytes mature into their adult form; inhibition of DUSP5 in adult hearts permits cell cycle progression in response to $T_3$.

DUSP5 Expression in Cardiomyocytes is Independent of Cell Maturation

Figure 6A:
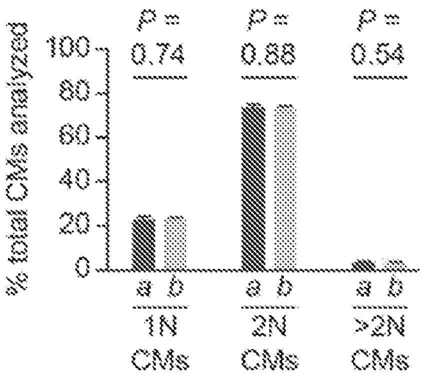
FIG. 6A shows data indication cardiomyocytes of the P8 LV apex and base have similar morphology. Comparison of mono-(1N), bi-(2N) and multi-nuclear (>2N) cardiomyocyte (CM) populations in the P8 LV apex (a) and base (b). Examples of mono-(1N), bi-(2N) and multi-nuclear (>2N) CMs are shown in insets, where CMs are identified by cTnT labeling and nuclei by DAPI.
Figure 6B:
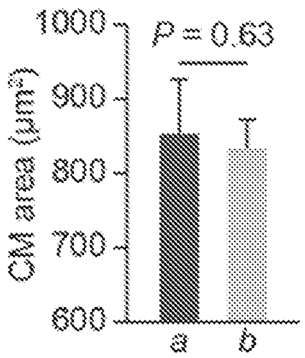
FIG. 6B shows a comparison of cell areas between P8 LV apical and base CMs.

Experiments were performed to determine if DUSP5 expression is secondary to cardiomyocyte maturation. Gene expression analyses revealed that DUSP5 mRNA levels were ~6-fold higher in cardiomyocytes of the P8 LV base than in those of the apex. However, no differences were seen in the expression of genes that regulate cardiomyocyte differentiation/dedifferentiation, oxidative phosphorylation, fatty acid synthesis, glycolysis, the DNA damage response or the cell cycle. Also, the distribution of mono-, bi- and multinucleated cardiomyocytes in these LV regions were similar (FIG. 6A) as were their sizes (FIG. 6B). These results indicate that DUSP5 expression in early post-neonatal LV cardiomyocytes is not related to a maturation-induced shift in metabolism, activation of the DNA damage response pathway, or cellular morphology.

Beta1-Adrenergic Receptors Promote DUSP5 Expression in Cardiomyocytes

Figure 7A:
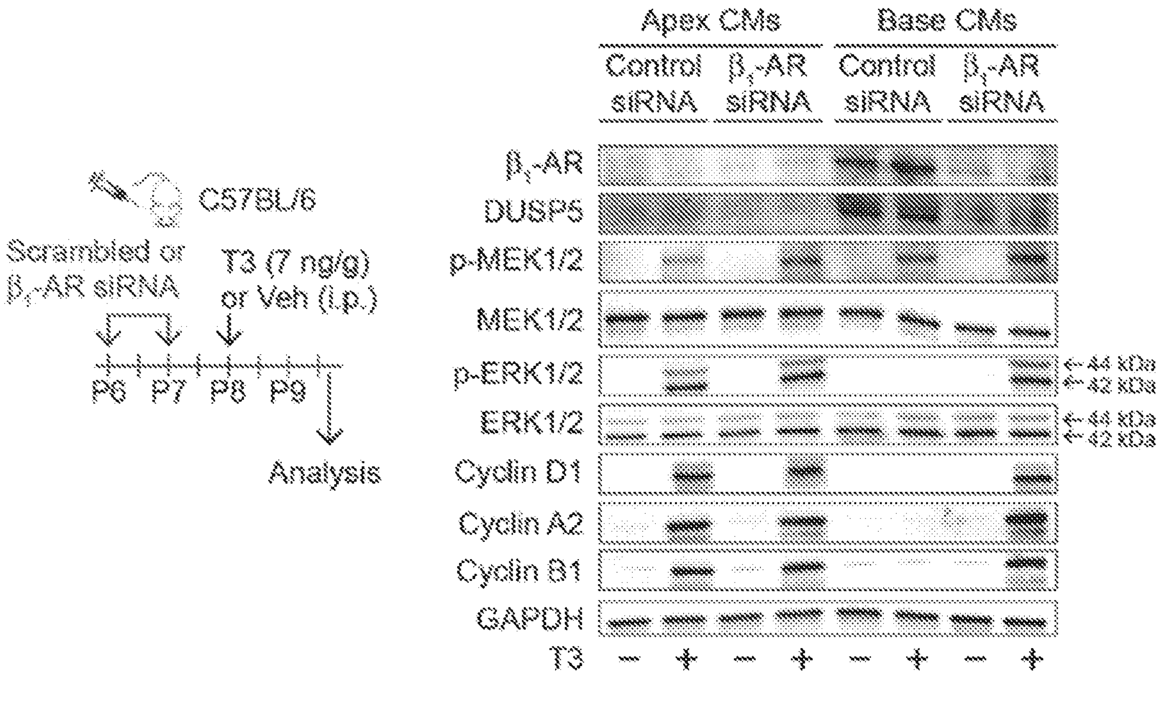
FIG. 7A. β1-adrenergic receptors (β1-AR) regulate DUSP5 expression in LV cardiomyocytes. β1-adrenergic receptor knockdown in cardiomyocytes of the early post-neonatal LV apex and base, using acute in vivo siRNA treatment, decreased DUSP5 levels and increased ERK1/2 phosphorylation and cyclin expression in response to $T_3$. Scrambled siRNA was used as a siRNA control.
Figure 7B:
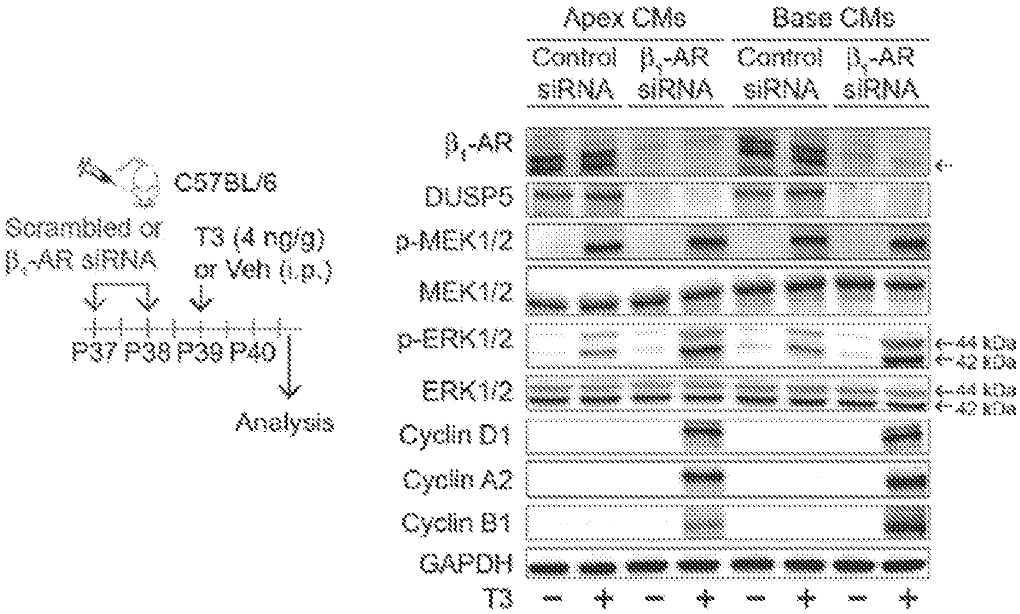
FIG. 7B shows data for 5-week-old mice.
Figure 7C:
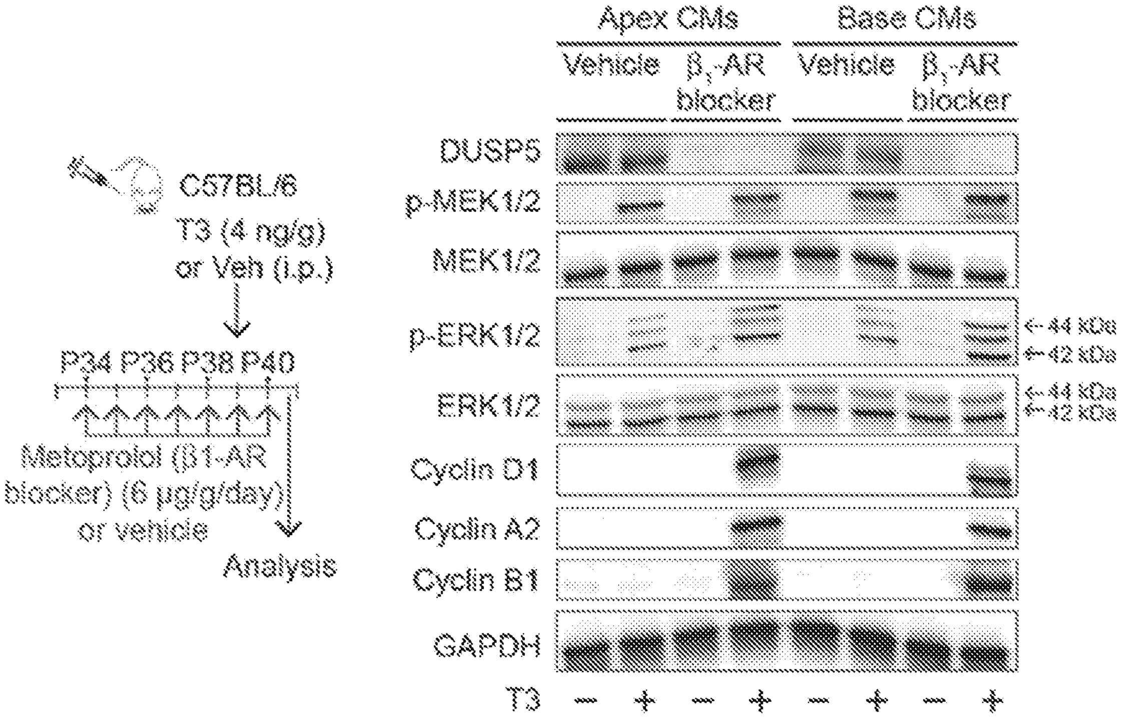
FIG. 7C shows data using a β1-AR blocker (metoprolol) pretreatment also blocks DUSP5 expression in young adult cardiomyocytes of the LV apex and base and increased cyclin expression in response to $T_3$.

As cardiomyocytes mature, they gain sensitivity to norepinephrine by increasing the number of β1-adrenergic receptors; this enhanced sensitivity is associated with progressive innervation of the LV by sympathetic nerves. The cardiac-sympathetic axis becomes functional after the first week of life. Experiments were performed to determine whether β1-adrenergic receptors regulate DUSP5 in LV cardiomyocytes. Sequential analyses, between P1 and P16, show associated developmental changes in LV β1-adrenergic receptors, adrenergic nerves (using tyrosine hydroxylase as a marker) and DUSP5 (FIG. 5A). To establish causality, β1-adrenergic receptors were knocked-down in vivo in early post-neonatal and young adult LV cardiomyocytes, using β1-adrenergic receptor siRNA, which inhibited cardiomyocyte DUSP5 expression and increased $T_3$-induced ERK1/2 phosphorylation (FIGS. 7A and 7B). DUSP5 expression was also suppressed after β1-adrenergic receptor blocker pretreatment with metoprolol; this pretreatment permitted the expression of cyclins D1/A2/B1 in response to $T_3$ (FIG. 7C). These results indicate that β1-adrenergic receptors regulate DUSP5 expression in LV cardiomyocytes. Moreover, they suggest that as sympathetic innervation extends during postnatal development from the LV base to its apex, it progressively triggers and then maintains cell cycle block in cardiomyocytes via β1-adrenergic receptor-mediated DUSP5 expression.

$T_3$ Stimulates Cardiac Muscle Formation in β1-Adrenergic Receptor Blocker Treated Mice Experiments indicate reversal of cell cycle block in cardiomyocytes is not sufficient for the activation of proliferation. Rather, a pro-proliferative stimulus is needed to get these cells to replicate. Experiments were performed to determine whether reversal of cell cycle block using β1-blockade coupled with acute $T_3$ treatment may be sufficient to expand the cardiomyocyte endowment of the adult murine heart. Adult mice (26-week-old) were given metoprolol (6 μg/g, daily, i.p.) or vehicle for 19 days; over the last 5 days of this β1-blockade (or vehicle control) the mice were additionally given $T_3$ (2 ng/g, daily, i.p.) or vehicle. Two weeks after cessation of these therapies LV dimensions and contractility were analyzed by echocardiography as well as ventricular cardiomyocyte numbers. The data are summarized in Table 1 below.

TABLE 1

Comparison of Echocardiography Dimensions and LV Systolic Function in Adult 6-Month-Old Mice given $T^3$ and Metoprolol Monotherapies or $T^3$ + Metoprolol Combination Therapy

| | No therapy* | T3 monotherapy* | Metoprolol monotherapy* | T3 + Metoprolol combination therapy* |
|---|---|---|---|---|
| Echocardiography, n | 19 | 20 | 20 | 20 |
| FW diastole, mm | 0.84 ± 0.02 | 0.87 ± $0.01^{NS}$ | 0.92 ± 0.02 | 1.01 ± 0.02 **** |
| FW systole, mm | 1.13 ± 0.03 | 1.19 ± $0.03^{NS}$ | 1.20 ± 0.03 | 1.33 ± 0.03 ** |
| IVS diastole, mm | 0.95 ± 0.01 | 0.94 ± $0.01^{NS}$ | 0.96 ± 0.02 | 1.09 ± 0.02 ** |
| IVS systole, mm | 1.31 ± 0.03 | 1.29 ± $0.02^{NS}$ | 1.29 ± 0.02 | 1.43 ± 0.03 *** |
| LV end-diastolic dimension, mm | 3.53 ± 0.06 | 3.60 ± $0.03^{NS}$ | 3.53 ± 0.07 | 3.66 ± $0.06^{NS}$ |
| LV end-systolic dimension, mm | 2.72 ± 0.07 | 2.70 ± $0.05^{NS}$ | 2.71 ± 0.06 | 2.25 ± 0.07 *** |
| Fractional shortening, % | 23.0 ± 1.4 | 24.8 ± $1.4^{NS}$ | 23.4 ± 0.6 | 38.5 ± 1.5 *** |
| Ejection fraction, % | 53.5 ± 1.5 | 55.7 ± $1.4^{NS}$ | 55.4 ± 1.8 | 78.0 ± 2.2 *** |
| LV mass, mg | 109 ± 2 | 110 ± $2^{NS}$ | 113 ± 2 | 141 ± 3 **** |
| Body weight, g | 33.3 ± 0.4 | 32.9 ± $0.4^{NS}$ | 33.2 ± 0.5 | 33.1 ± $0.3^{NS}$ |
| Euthanasia, n | 9 | 8 | 9 | 7 |
| Cardiomyocyte numbers, (millions) [n] | 2.37 ± 0.029 | 2.33 ± $0.039^{NS}$ | 2.44 ± 0.026 | 2.88 ± 0.056* |

*Six-month-old mice were given metoprolol (6 μg/g daily, i.p.) or vehicle (as control) pretreatment for 19 days. On day-14 of this therapy, they were additionally given 5 daily injections of $T_3$ (2 ng/g, i.p.) or vehicle. At 2 weeks after the cessation of mono- or combination therapy body weights of these mice were determined, and their cardiac dimensions and function determined by transthoracic echocardiography.

In vehicle pretreated mice, $T^3$ treatment did not significantly affect body weight, ventricular cardiomyocyte numbers, LV mass or any measured LV dimension. By contrast, in metoprolol-treated mice, $T_3$ treatment increased ventricular cardiomyocyte numbers by 18% (that is, by ~450,000 cardiomyocytes) (P<0.001), LV mass by 25% (P<0.001), and LV free wall dimension at diastole by 11% (P<0.001), without significantly changing LV end-diastolic dimension. These functional parameters are consistent with heart growth without chamber occlusion. Metoprolol/$T_3$ treatment did not increase mortality—no animals died as a result of this therapy—or influence body weight. The most striking effect of the combination therapy, relative to metoprolol monotherapy, was an about 40% increase in ejection fraction (P<0.001) which, in a cohort of animals given combination therapy, was mostly sustained over the 4-week post-therapy follow up interval (ejection fraction: 83.6%±1.04% and 82.4%±1.05% at 2 and 4 weeks after cessation of combination therapy, respectively; number of pairs=8; P=0.031, paired 2-tailed Student's t-test).

What is claimed is:

1. A method of treating or preventing a heart malformation or cardiovascular disease comprising administering an effective amount of thyroid hormone in combination with a DUSP5 inhibitor and optionally a beta-adrenergic blocking agent to a subject in need thereof, wherein the DUSP5 inhibitor is an siRNA duplex of GCAUGGCUUACCUUAUGAATT (SEQ ID NO: 111) and UUCAUAAGGUAAGCCAUGCTT (SEQ ID NO: 112).

2. A method of treating or preventing a heart malformation or cardiovascular disease comprising administering an effective amount of thyroid hormone in combination with a DUSP5 inhibitor and optionally a beta-adrenergic blocking agent to a subject in need thereof, wherein the DUSP5 inhibitor is an siRNA duplex of CGUCUAGUUGGGAAAGUAATT (SEQ ID NO: 113) and UUACUUUCCCAACUAGACGTT (SEQ ID NO: 114).

3. A method of treating or preventing a heart malformation or cardiovascular disease comprising administering an effective amount of thyroid hormone in combination with a DUSP5 inhibitor and optionally a beta-adrenergic blocking agent to a subject in need thereof, wherein the DUSP5 inhibitor is an siRNA duplex of GUAGCAAGAUGUUGGCUUUTT (SEQ ID NO: 115), and AAAGCCAACAUCUUGCUACTT (SEQ ID NO: 116).

4. The method of claim 3, wherein thyroid hormone and the DUSP5 inhibitor is administered in combination with a beta-adrenergic blocking agent selected from acebutolol, atenolol, betaxolol, bisoprolol, carteolol, carvedilol, esmolol, labetalol, metoprolol, nadolol, nebivolol, penbutolol, pindolol, propranolol, sotalol, and timolol, or salts thereof.

5. The method of claim 3, wherein the DUSP5 inhibitor is administered in combination with a mitogen.

6. The method of claim 5, wherein the mitogen is neuregulin, IGF-1, YAP1, or ERBB2.

7. The method of claim 1, wherein thyroid hormone and the DUSP5 inhibitor is administered in combination with a beta-adrenergic blocking agent selected from acebutolol, atenolol, betaxolol, bisoprolol, carteolol, carvedilol, esmolol, labetalol, metoprolol, nadolol, nebivolol, penbutolol, pindolol, propranolol, sotalol, and timolol, or salts thereof.

8. The method of claim 1, wherein the DUSP5 inhibitor is administered in combination with a mitogen.

9. The method of claim 8, wherein the mitogen is neuregulin, IGF-1, YAP1, or ERBB2.

10. The method of claim 2, wherein thyroid hormone and the DUSP5 inhibitor is administered in combination with a beta-adrenergic blocking agent selected from acebutolol, atenolol, betaxolol, bisoprolol, carteolol, carvedilol, esmolol, labetalol, metoprolol, nadolol, nebivolol, penbutolol, pindolol, propranolol, sotalol, and timolol, or salts thereof.

11. The method of claim 2, wherein the DUSP5 inhibitor is administered in combination with a mitogen.

12. The method of claim 11, wherein the mitogen is neuregulin, IGF-1, YAP1, or ERBB2.

* * * * *